(12) United States Patent
Louis

(10) Patent No.: US 7,686,281 B2
(45) Date of Patent: Mar. 30, 2010

(54) STAPLE REMOVER

(75) Inventor: Pan Louis, Chatswood (AU)

(73) Assignee: Louis Pan, North, NSW (AU)

( * ) Notice: Subject to any disclaimer, the term of this patent is extended or adjusted under 35 U.S.C. 154(b) by 585 days.

(21) Appl. No.: 10/529,297

(22) PCT Filed: Aug. 3, 2004

(86) PCT No.: PCT/AU2004/001026

§ 371 (c)(1),
(2), (4) Date: Mar. 25, 2005

(87) PCT Pub. No.: WO2006/012666

PCT Pub. Date: Feb. 9, 2006

(65) Prior Publication Data

US 2007/0040155 A1    Feb. 22, 2007

(51) Int. Cl.
*B25C 11/00* (2006.01)
(52) U.S. Cl. .................................................. 254/28
(58) Field of Classification Search ............... 254/28, 254/18, 25, 21, 30
See application file for complete search history.

(56) References Cited

U.S. PATENT DOCUMENTS

| | | | |
|---|---|---|---|
| 1,948,096 A | 2/1934 | Cavanagh | |
| 2,481,647 A | 9/1949 | De Generes | |
| 2,499,432 A | 3/1950 | Von Cseh | |
| 5,195,724 A * | 3/1993 | Koo | 254/28 |
| 5,605,320 A * | 2/1997 | Crawford | 254/28 |
| 5,653,424 A * | 8/1997 | Khan | 254/28 |
| 5,657,965 A * | 8/1997 | Arias | 254/28 |
| 5,996,969 A * | 12/1999 | Johnston et al. | 254/28 |
| 6,772,996 B1 * | 8/2004 | Carlson et al. | 254/28 |

* cited by examiner

*Primary Examiner*—Lee D Wilson

(57) ABSTRACT

The base member 1 is pivotally connected to the lever member 2 by a pin 5 that provides a leverage fulcrum point. The tongue 3 extends from the front end of the base member 1 and is used to wedge under the staple crossbar 11. The teeth 4 extends from the front end of the lever member 2. The user then lifts the lever member 2 into a second position so that the wider top section 8 of teeth 4 lifts the staple 10 from the substrate. The front edges 9 of teeth 4 are curved such that it does not go below the baseline of base member 1, and thus do not interfere with or damage the substrate. The base member 1 presses against substrate providing support and allows the leverage operation to be performed on pliable and flexible substrates such as sheets of paper, and minimizes damage to the substrate.

29 Claims, 20 Drawing Sheets

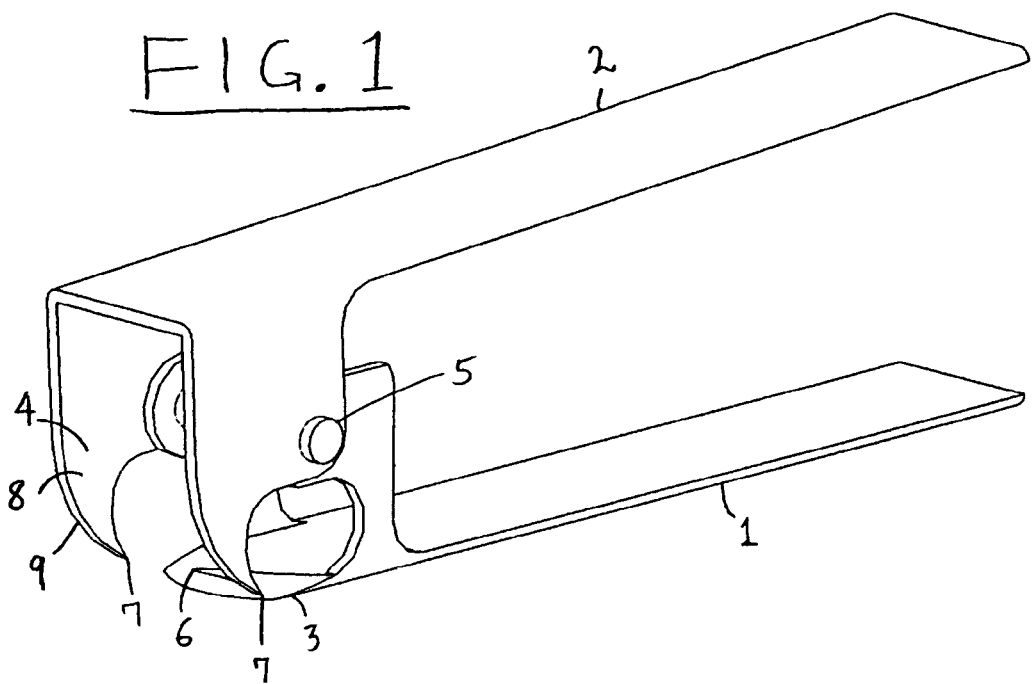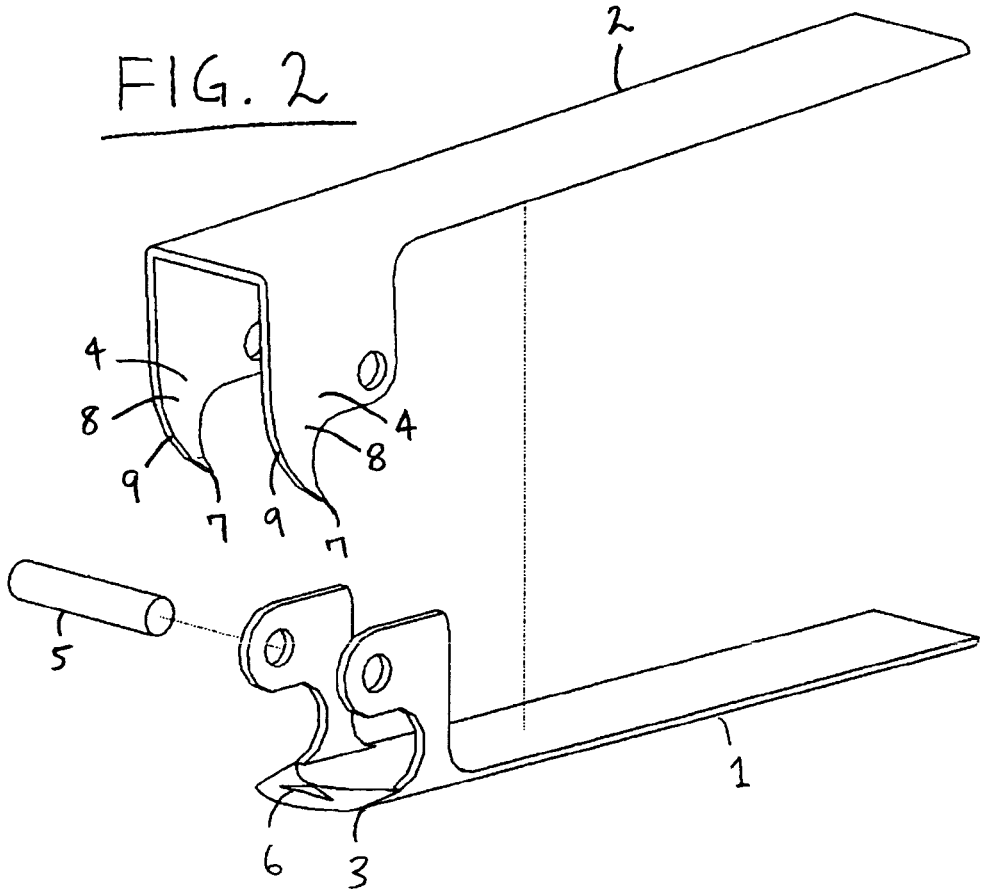

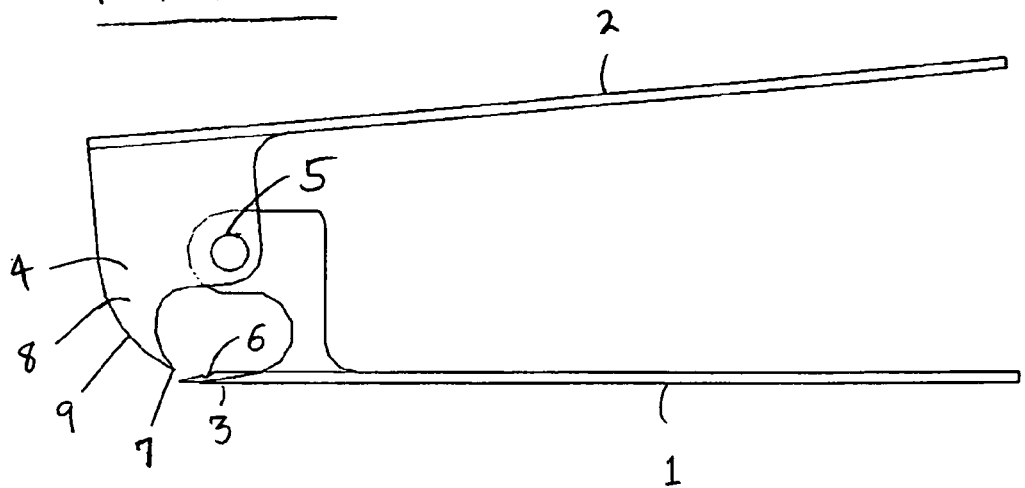
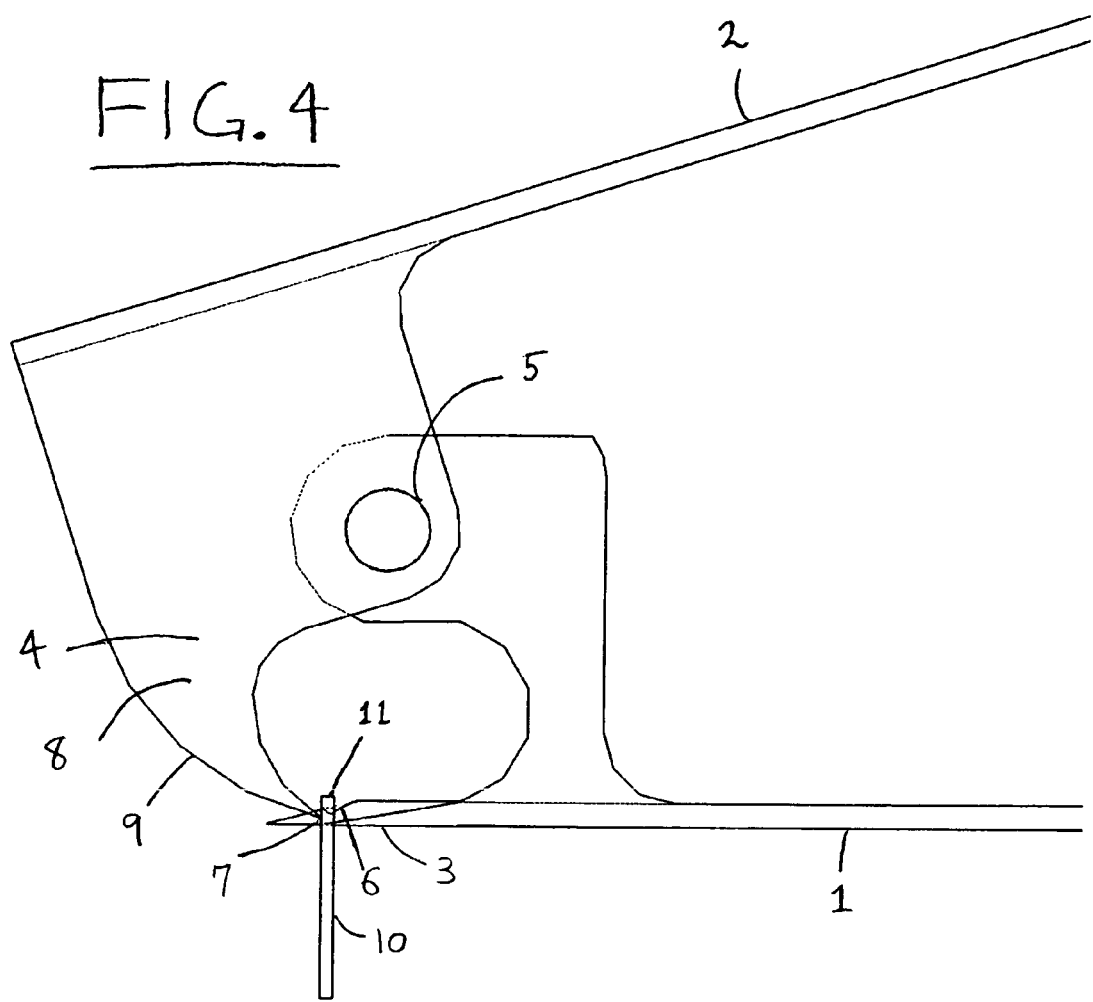

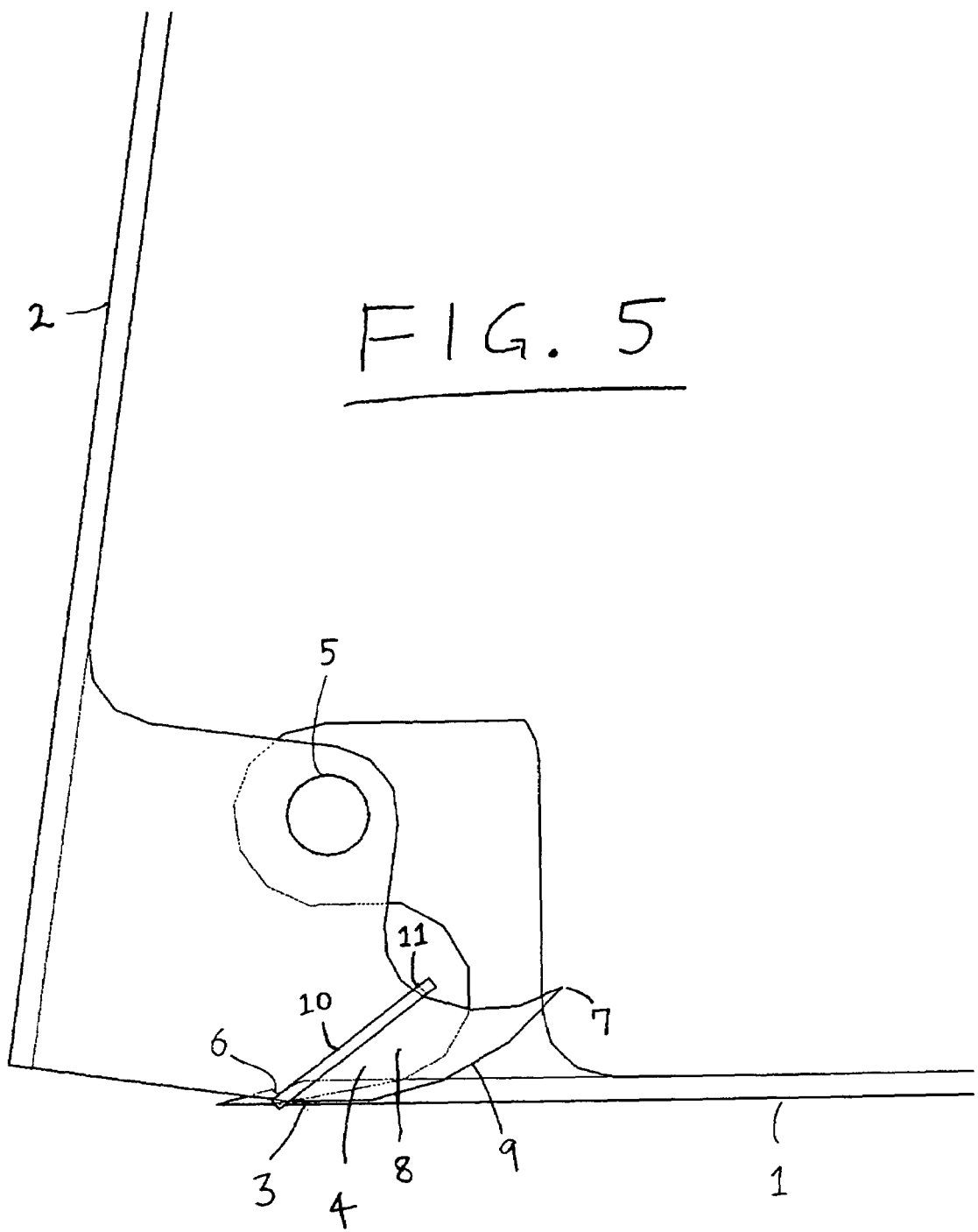

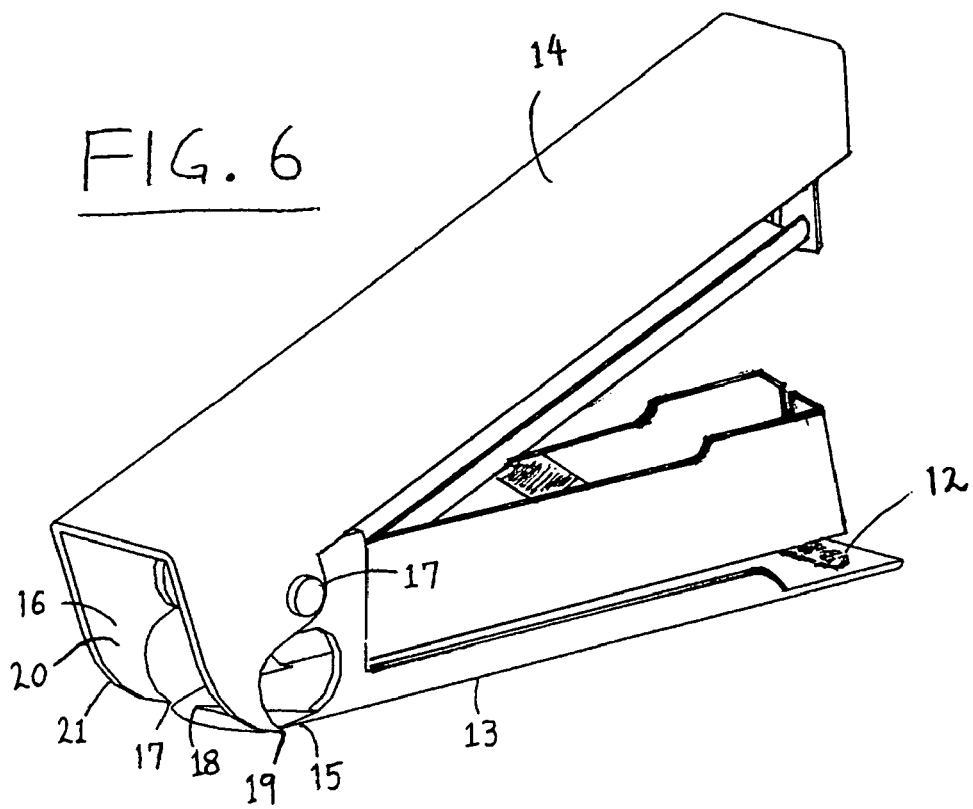
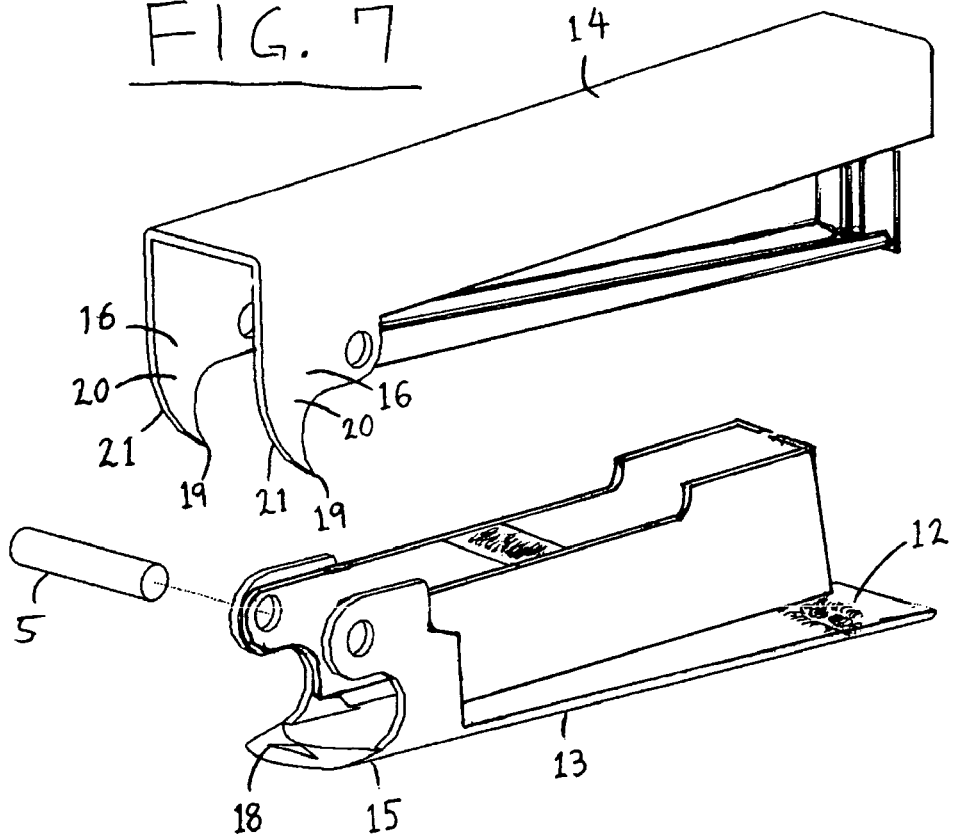

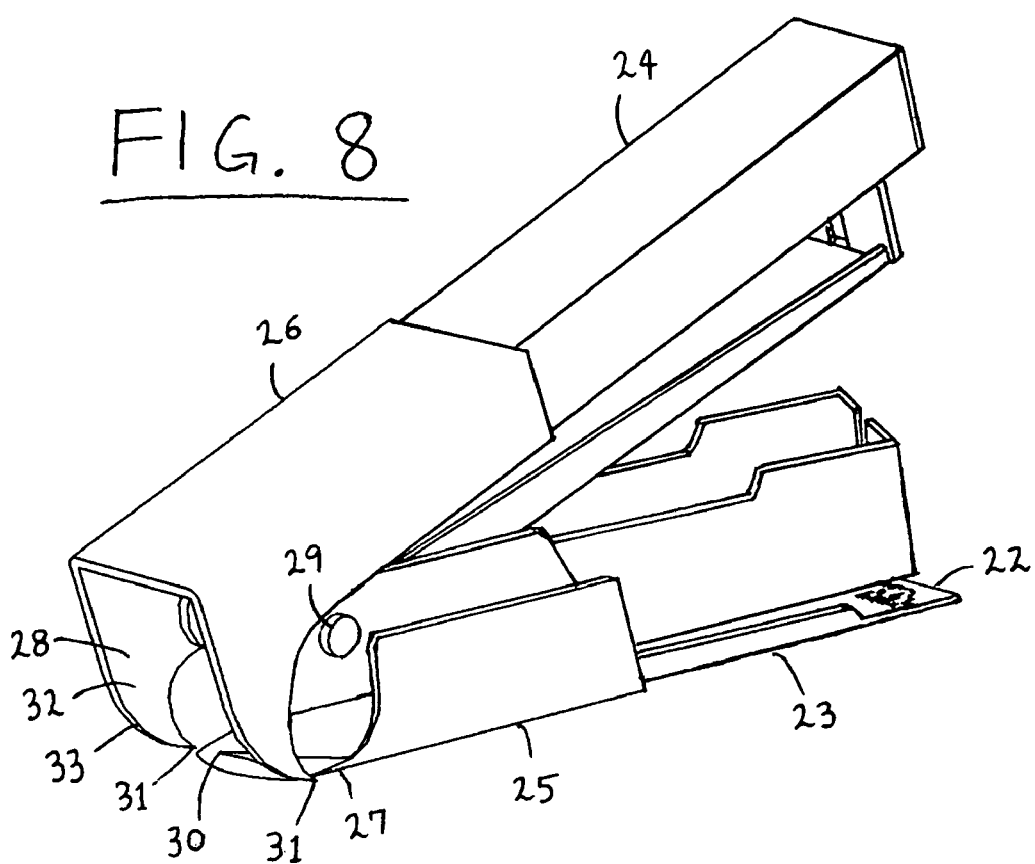
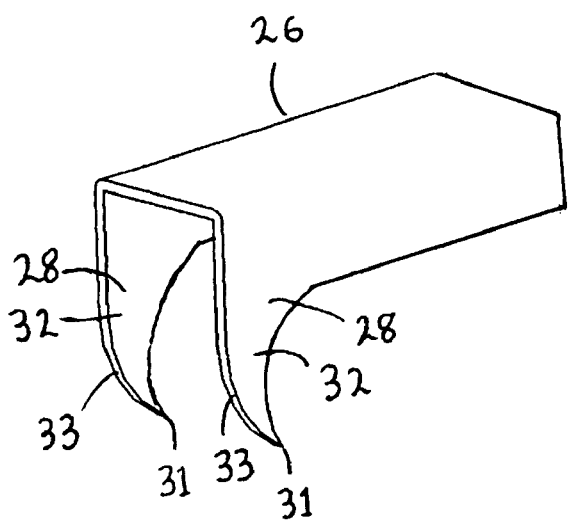
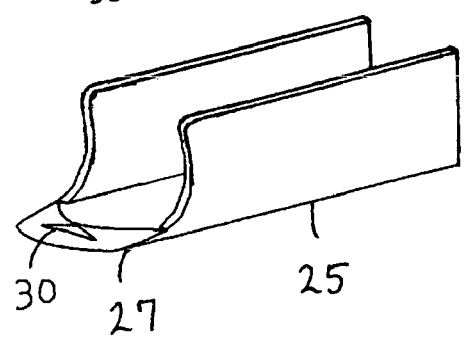

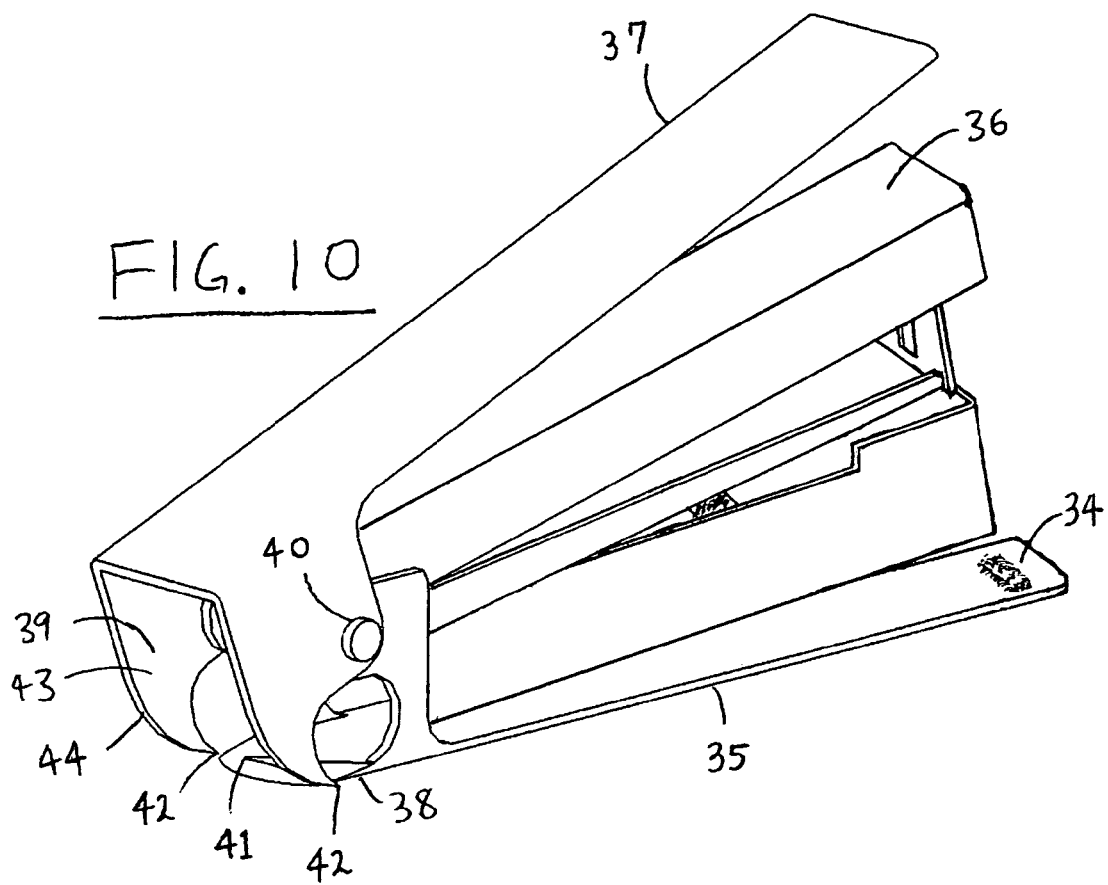

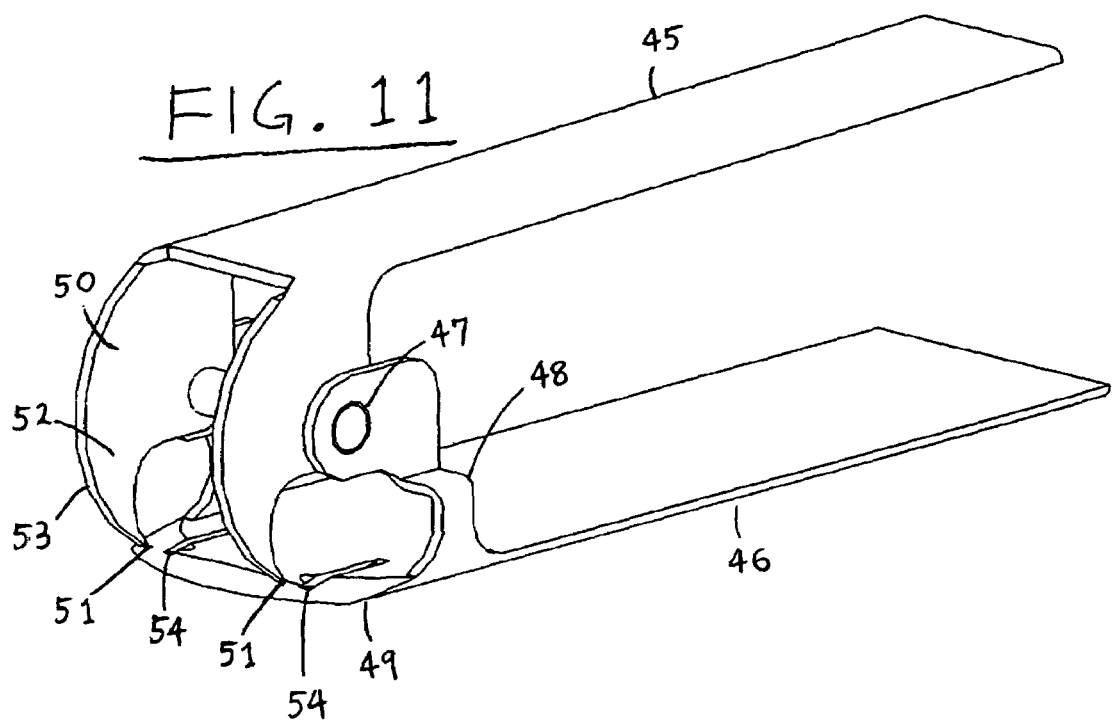
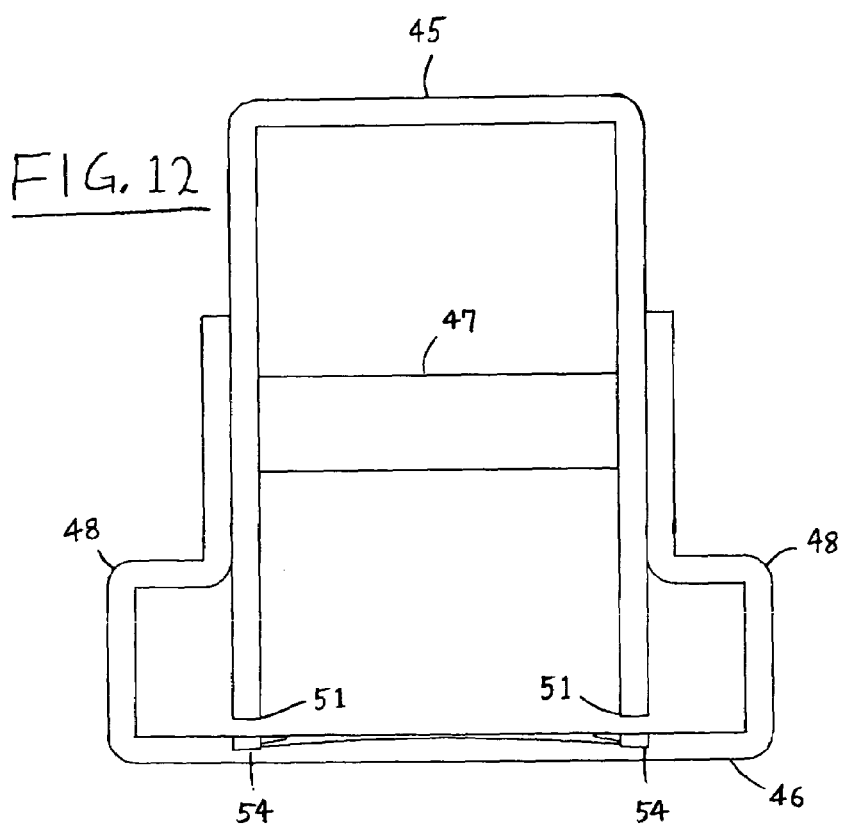

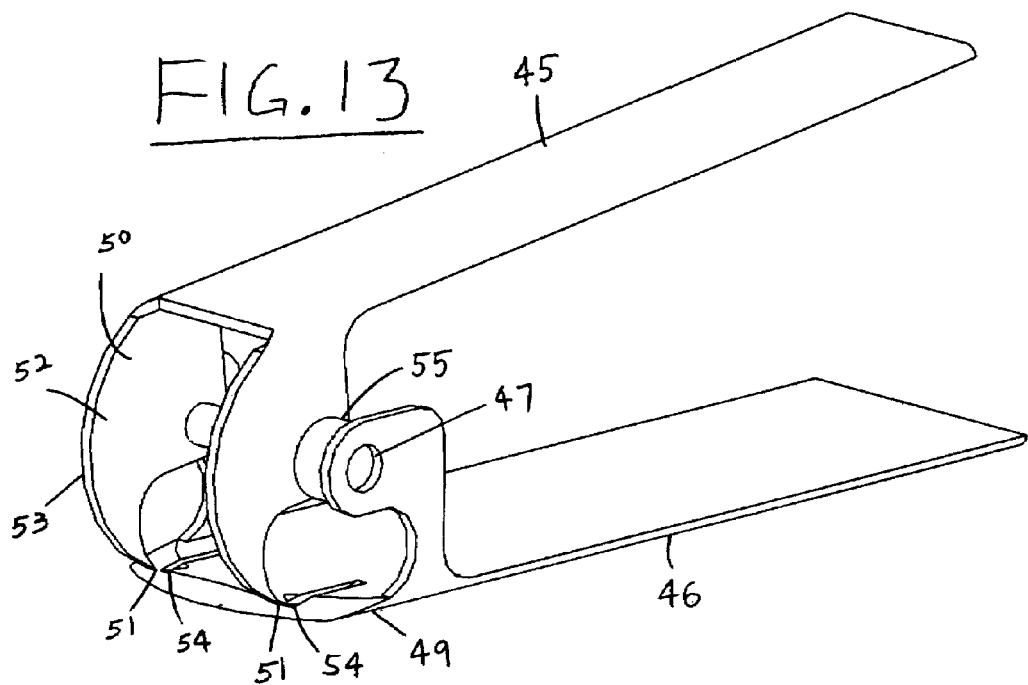
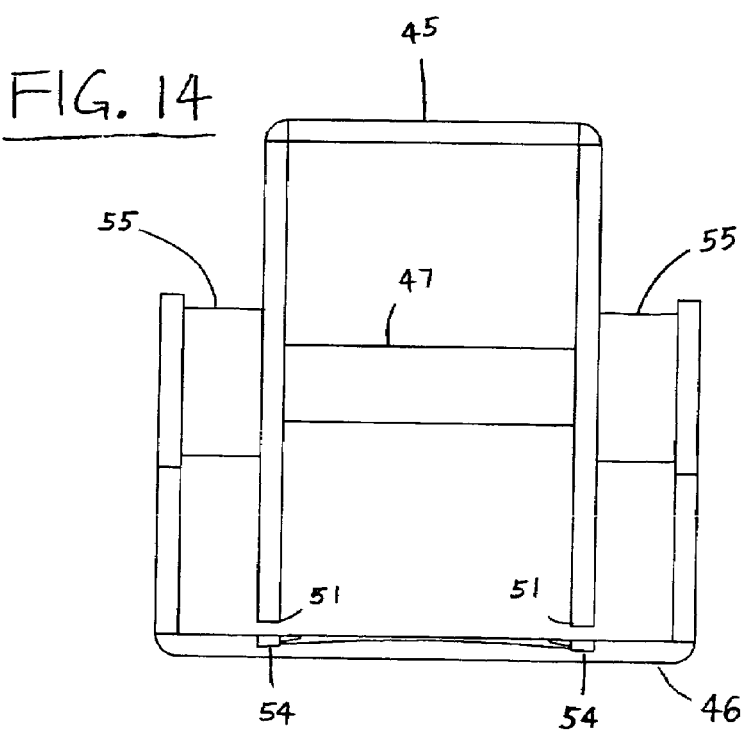

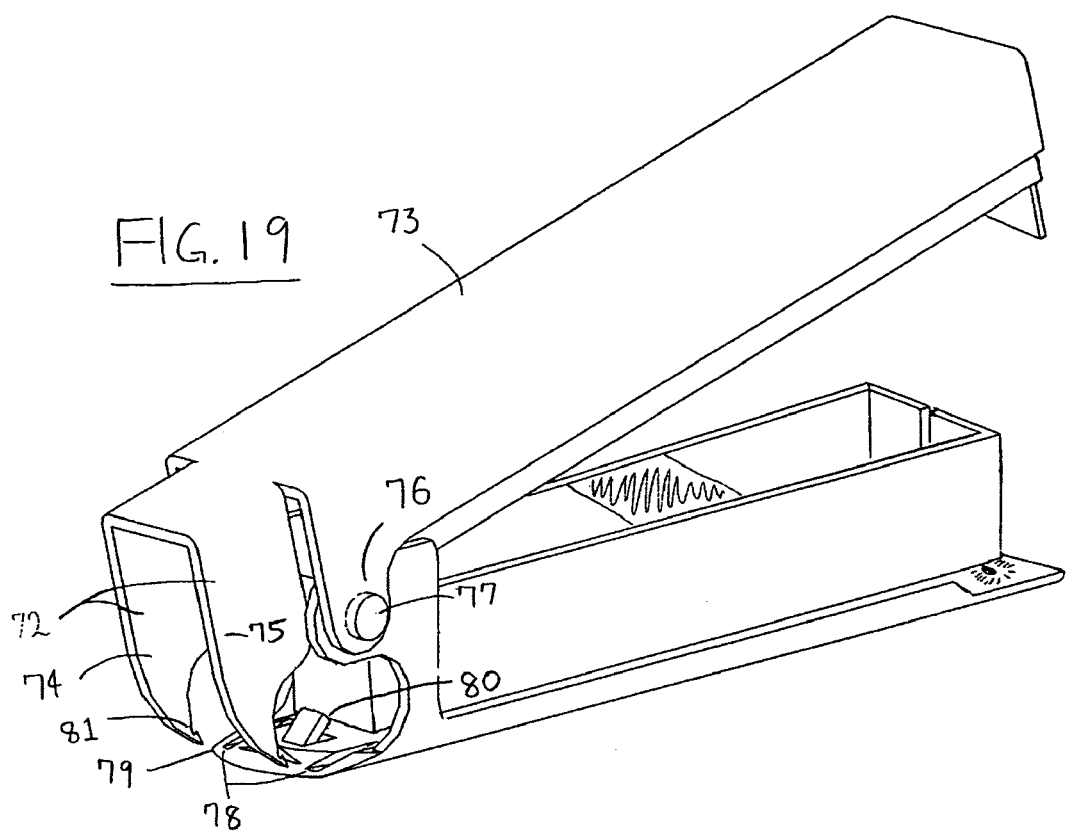
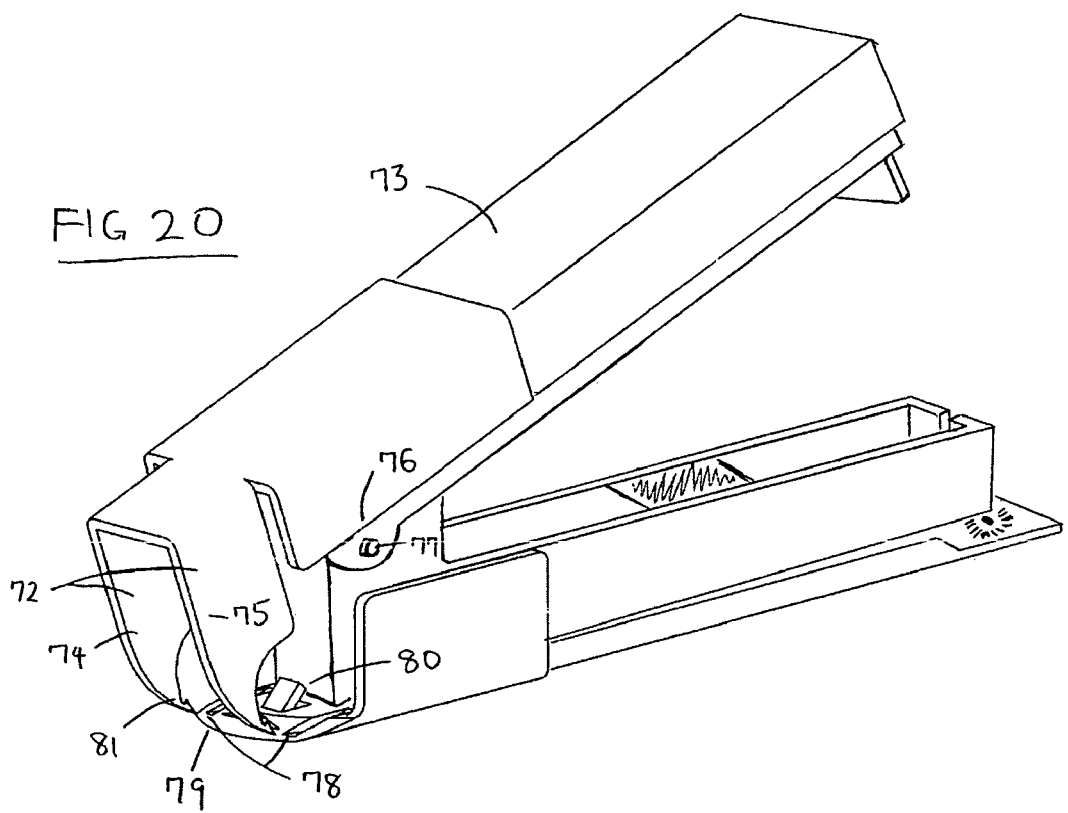

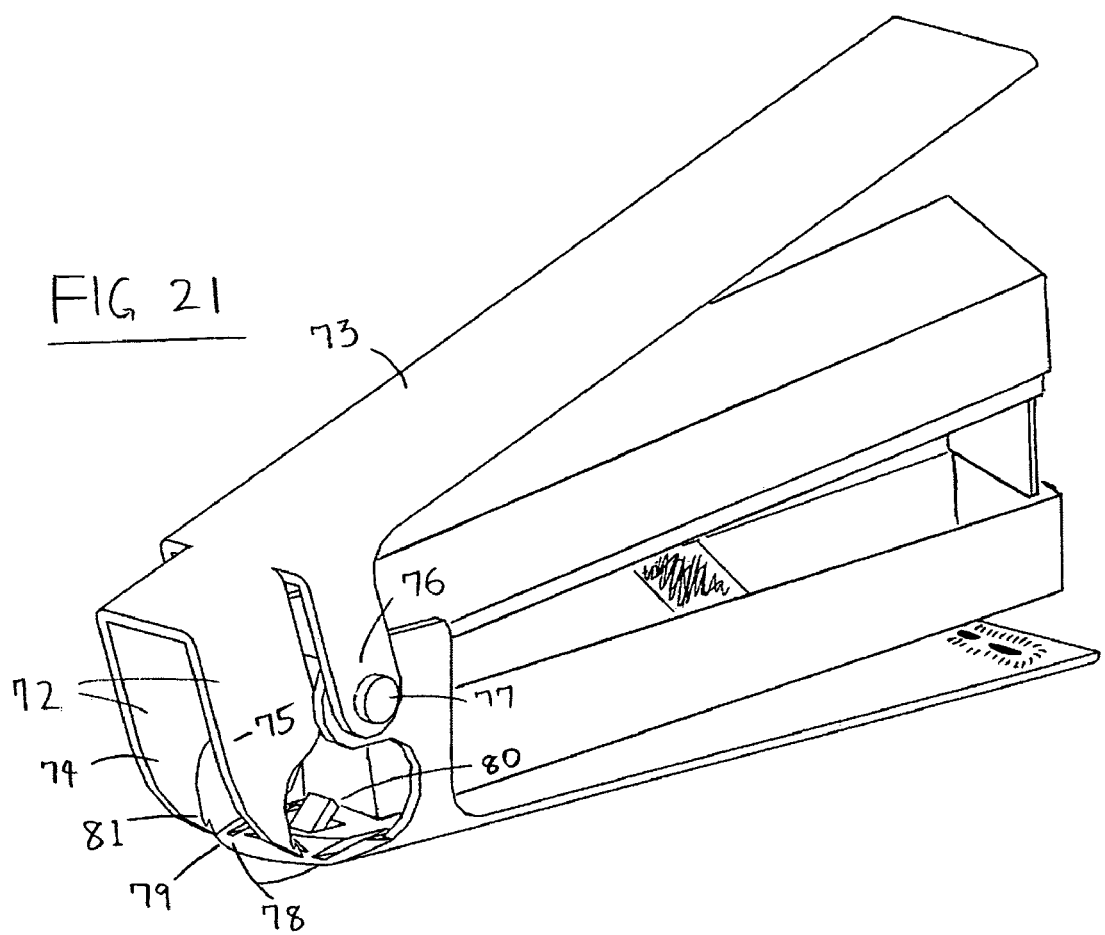

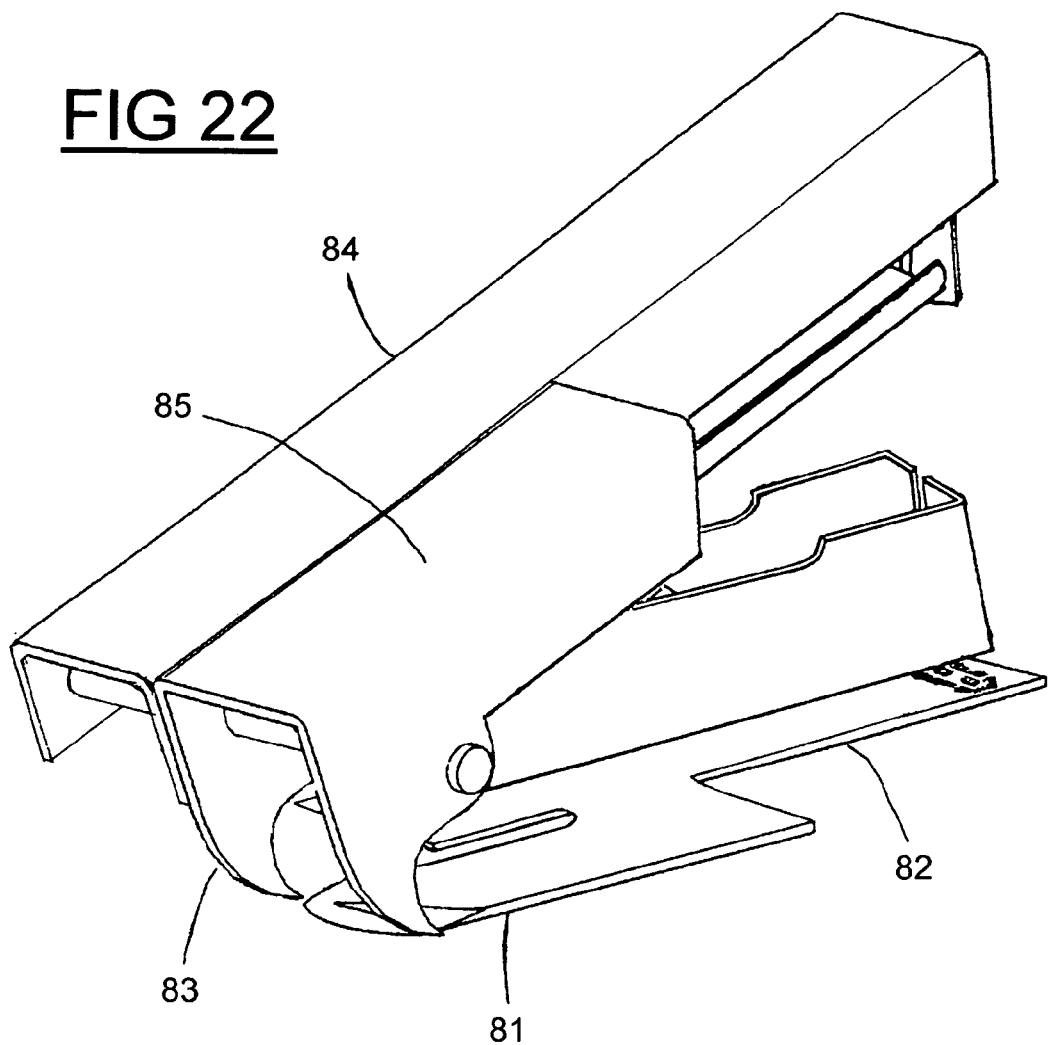

STAPLE REMOVER

FIELD OF THE INVENTION

This invention relates to an apparatus for removing staples from a stack of sheet materials or from a solid substrate.

BACKGROUND OF THE INVENTION

There is a growing need for staple removing devices, as staplers is now a popular consumer item. Many people use staplers, from builders, office workers, students at school, to the people at home. While stapling sheets or solid substrates such as wood, there are times when the staple needs to be removed because the staple is stapled in the wrong place, or there was a need to add more sheets, or was not stapled properly such that staple was warped and would not hold properly.

Many devices were created to remove staples. A pry type staple remover uses a chisel-like tongue to wedge under the staple's arms to twist and dig the arms up, and the tongue is wedged under the staple crossbar to lift and dig the whole staple up. Removing the staples in this fashion requires a lot of time, a large number of actions, and it usually damages the substrate. Also, it is sometimes unsuccessful in completely removing the staple, requiring fingernails or pliers to complete the job.

A double jawed pincer type staple remover uses a pair of opposed arms with curved teeth members that wedges under the staple crossbar to lift staple up. This type of remover suffers from a disadvantage of requiring a large amount of force to operate because the operator has to press the arms together at the position where there is no mechanical leverage advantage from the opposed arms. Thus this remover is only useful for small office type staples, and not heavy-duty staples. This large force results in unpredictable behavior, since a small variation in the angle of application will result in uneven forces distributed across staple crossbar so that only one arm is removed. Also, when the substrate is especially thing and pliable, such as in the case of only a few sheets stapled together, removing the staple using the double jawed pincer type often makes a mess of the substrate and tears the substrate with the staple still attached to the torn pieces of substrate.

U.S. Pat. No. 5,195,724 issued on Mar. 23, 1993 to Koo, U.S. Pat. No. 5,657,965 issued on Aug. 19, 1997 to Aria, and U.S. Pat. No. 6,772,996 issued on Aug. 10, 2004 to Carlston et al. all describe staple removing devices with similar staple removing principles, the double jawed pincer type staple remover described above. Staple removers using this principle have the disadvantage of requiring high amount of manual force from the fingers to operate. These types of staple removers also have the disadvantage of in inadequate support to the substrate. Due to the high and difficult to control forces required from the fingers, and from the many moving parts moving in contact with the substrate, the paper is frequently damaged during the staple removing operation.

U.S. Pat. No. 5,605,320 issued on Feb. 25, 1997 to Crawford describes a staple remover having a first member with two spaced apart prongs inserted under the staple crossbar, and a second member pivotally connected to the first member, and a nose member. The nose member, upon relative movement between the first and second member, deforms the staple to allow the staple legs to be withdrawn substantially from the substrate. This type of staple remover also suffers from inadequate support to the substrate. The substrate is frequently dented and damaged by the nose member when the said nose member moves below the two spaced apart prongs and into the substrate. At the same time, the substrate near the staple legs is also damaged due to inadequate support, because the two spaced apart prongs are lifted from the substrate to naturally oppose the nose member as it presses into the substrate.

U.S. Pat. No. 5,996,969 issued in Dec. 7, 1999 to Johnston et al, describes a staple remover including a clamping mechanism that secures one staple leg to the remover, enabling extracting of that leg. The staple is removed by prying and lifting, similar to the pry-type remover described above. The prying action naturally produces a gap between the staple and substrate, and therefore also suffers from the disadvantage of inadequate support to fragile substrates such as paper.

U.S. Pat. No. 5,653,424 issued on Aug. 5, 1997 to Khan, describes a staple remover with a tongue-like tapered blade and a slidable claw member. The blade is slidably inserted under the staple arm causing the staple to unclenth. A slidable claw member is used to push the staple into a storage compartment. This staple remover requires the remover to slide a relatively long distance until the wider end of the tapered tongue unclenches the staple.

A levered pry type stapler remover uses a tongue extending from a lever member pivotally connected to a base member to wedge under the staple crossbar. Pushing down the lever member forces the tongue upwards, lifting the staple from the substrate. However, this type of remover does not do anything to prevent the substrate from being damaged or torn.

Thus it is desirable to have a staple removing device that does not require excessive force to operate, minimises damage to the substrate, and doesn't require sliding the remover long distances.

SUMMARY OF THE INVENTION

In accordance with the present invention, an improved staple remover comprising:
- a base member having a front end, a rear end, and a first section near the front end;
- a lever member having a front end, a rear end, and a first section near the front end, the said first section of the lever member is pivotally attached to the first section of the said base member;
- a tongue;
- means of lifting the staple from the substrate using the leverage from the lever member pivotally attached to the base member, where the said lifting means does not extend below the baseline of the said base member during the staple removing operation;
- means of supporting and continuing to support the substrate throughout the staple removing operation with the said base member, is provided.

In the preferred embodiment of the invention, the said tongue extends from the base member and is used to wedge under the staple crossbar. The means of lifting the staple from the substrate comprises of teeth which extends from the lever member, such that when the lever member is operated from a first position to a second position, the said teeth engages the underside of the staple crossbar and lifts it from the substrate.

The present invention offers the user an easier way of removing staples by using leverage. The tongue provides support, allowing the leverage operation to be performed on pliable and flexible substrates such as sheets of paper, and minimizing damage to the substrate.

Additionally, the present invention can be combined with a stapler, either as an integrated part of the stapler, or attached to the stapler as attachments. This gives an additional benefit of making the staple removing device more accessible to the user, and preventing it from being easily misplaced. While the user is stapling, if a need to remove staples arises, the user will no longer need to look for a separate device to remove the staples.

The present invention can be made from metal sheets, punched into the appropriate shape, and then bent into the appropriate form, thus it should not be expensive to manufacture. In the case where the present invention integrated with a stapler, since the same manufacturing processes to make the staple driving lever and the stapler base can be used to also make the base member and the lever member of the present invention, it should not add significantly to the cost of a normal stapler.

The present invention can be used to remove staples from pliable substrates such as sheets of paper, or solid substrates such as wood.

The above preferred embodiment and other variations and advantages of the present invention will become apparent to those skilled in the art upon a more detailed description of the invention.

BRIEF DESCRIPTION OF DRAWINGS

FIG. 1 is a perspective view of the preferred embodiment of the invention

FIG. 2 is an exploded perspective view of the preferred embodiment of the invention.

FIG. 3 is a side view of the preferred embodiment of the invention in the first position.

FIG. 4 is an enlarged side view of the head section of the preferred embodiment of the invention at the point where a staple is about to be lifted.

FIG. 5 is an enlarged side view of the head section of the preferred embodiment of the invention at the point where a staple is completely removed.

FIG. 6 is a perspective view of an embodiment of the invention combined with a stapler.

FIG. 7 is an exploded view of an embodiment of the invention combined with a stapler.

FIG. 8 is a perspective view of an embodiment of the invention attached to a stapler.

FIG. 9 is a perspective view of the attachments.

FIG. 10 is a perspective view of an embodiment of the invention housed around a stapler.

FIG. 11 is a perspective view of an embodiment of the invention where the lever member fits inside the base member, and where the base member is bent to provide a gap for the removed staple.

FIG. 12 is the front view of the embodiment of the invention where the lever member fits inside the base member, and where the base member is bent to provide a gap for the removed staple.

FIG. 13 is a perspective view of an embodiment of the invention where the lever member fits inside the base member, and where washers are used to provide a gap for the removed staple.

FIG. 14 is the front view of the embodiment of the invention where the lever member fits inside the base member, and where washers are used to provide a gap for the removed staple.

FIG. 19 shows another embodiment of the invention combined with a stapler with narrower teeth.

FIG. 20 shows another embodiment of the invention attached to a stapler.

FIG. 21 shows another embodiment of the invention housed around a stapler.

FIG. 22 shows another embodiment of the invention combined to the side of a stapler device.

DETAILED DESCRIPTION

Figure 15:
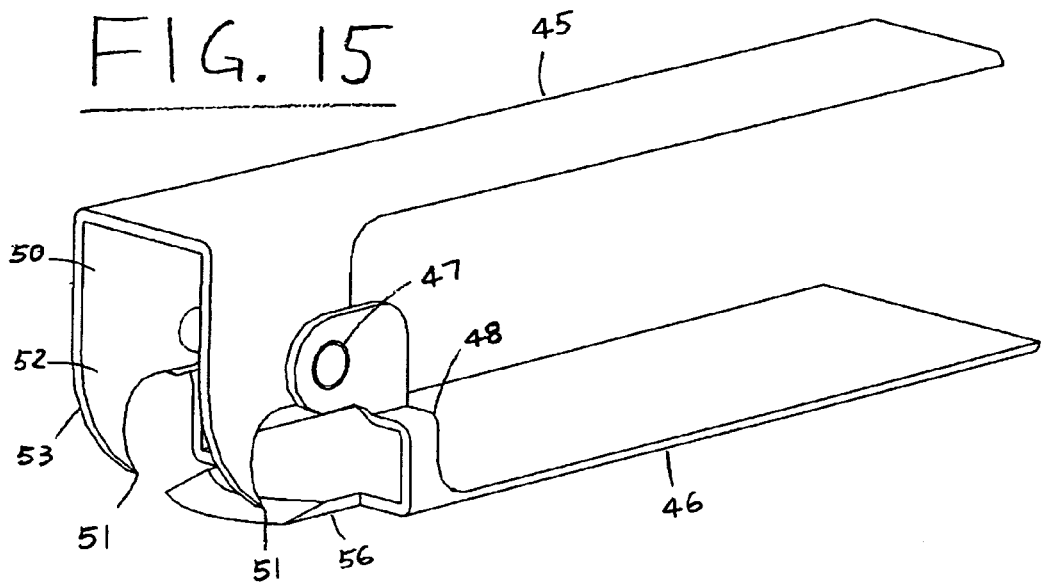
FIG. 15 shows an embodiment of the invention where the lever member fits inside the base member, and where instead of using grooves, the tongue made thinner.

Referring to FIG. 1, FIG. 2, FIG. 3, it can be seen that the preferred embodiment of the staple remover device according to this invention comprises of a base member 1, a lever member 2, a tongue 3, and teeth 4. The base member 1 is pivotally connected to the lever member 2 by a pin 5 that provides a leverage fulcrum point. It should be understood that other means of providing a fulcrum point for leverage such as rivets can be used for this invention, and is not limited to a pin. The tongue 3 extends from the front end of the base member 1 and is used to wedge under the staple crossbar. A groove 6 can be optionally etched, moulded or bent into tongue 3 to indicate the point where the staple needs to be wedged up to for removal. The teeth 4 extends from the front end of the lever member 2. The teeth 4 is narrow at tip 7 and wider at top section 8. FIG. 1 and FIG. 3 shows the lever member 2 is at a first position where the teeth 4 is above the tongue 3 providing room to wedge a staple above the tongue 3. The front edges 9 of the teeth 4 are curved in such a way that when the lever member 2 is moved into a second position where the tip 7 of teeth 4 is behind the staple point, the front edges 9 of the teeth 4 do not go below the baseline of the base member 1. The staple point is the point where the staple is stapled into the substrate.

FIG. 4 and FIG. 5 illustrates the staple remover device in operation. FIG. 4 demonstrates the point where the staple 10 is about to be lifted. Although not strictly required, for the easiest operation, the user should first wedge tongue 3 under the staple crossbar 11, to provide room to allow the tip 7 of teeth 4 to go below the staple crossbar 11. A less effective way is to use a shorter tongue which ends at the point where groove 6 would have been etched, so that the user only need to press the tongue against the side of the staple crossbar 11. This less effective method relies on a angled knife-like edge on the tip of the tongue and the tip 7 of the teeth 4 such that when both the said tongue and said teeth are pressed against the staple crossbar 11, coupled with the force of the staple removing device against the substrate, the likelihood is that both the teeth and tongue will both go under the staple crossbar 11.

The user then lifts the lever member 2 into a second position so that the wider top section 8 of teeth 4 lifts the staple 10 from the substrate, as shown in FIG. 5. The front edges 9 of teeth 4 are curved such that it does not go below the baseline of base member 1, and thus do not interfere with or damage the substrate.

The base member 1 presses against substrate at the point where the staple 10 is stapled into the substrate, thus providing support and enabling utilization of the mechanical leverage advantage from the lever member 2 pivotally attached to the base member 1. The support provided by the base member 1 allows the leverage operation to be performed on pliable and flexible substrates such as sheets of paper, and minimizes damage to the substrate.

During the staple removing operation, the user presses the rear end of base member 1 against the substrate. Throughout the staple removing operation, the base member 1 maintains contact and support of the substrate. This is because user only need to apply a downwards force on the base member 1 against the substrate, which is stabilized by the surface under the substrate; a destabilizing lifting force on the base member is not required; also, the large surface area of base member 1 in contact with the substrate increases the support to the substrate; finally, pressing down on the rear end of base member 1 utilizes leverage due the length of base member 1, reducing the amount of force required to stabilize the said base member 1.

The net forces will only result in the base member 1 moving in a direction parallel to the substrate. During this parallel movement, the base member 1 maintains contact with the substrate at all times; therefore it maintains support of the substrate. The parallel movement of the base member is desirable because it continues to wedge the tongue 3 further under the staple crossbar 11, until the upward force of the teeth 4 on the staple crossbar 11 removes the staple from the substrate.

During the staple removing operation, the tip 7 of teeth 4 will travel in a circular path when the user lifts the lever member, without going below the baseline of base member 1. Therefore, the tip 7 will be closest to the substrate at a point directly below the pivot pin 5. This means the tip 7 would normally only be able to engage the staple 10 when the staple is directly under the pivot pin 5. However, because the tongue 3 is wedged under the staple crossbar 11, it raises the staple crossbar 11 into the circular path of the tip 7 some distance away from the point directly below the pivot pin 5. FIG. 4 illustrates how the tip 7 of teeth 4 is able to engage under the raised staple crossbar 11 at a point some distance away from the point directly below the pivot pin 5.

The following describes variations of the present invention. The basic operation and principles of the present invention remains the same, allowing for variations that will be become clear in the descriptions.

FIG. 6 and FIG. 7 shows the present invention combined with a stapler device. All the necessary components of a stapler device will not be illustrated in this application, for two reasons: First, it is understood by the inventor that the manufacture of a stapler device is well known by those skilled in the art. Secondly, it will avoid confusion when describing the present invention combined with a stapler device. Referring to FIG. 6 and FIG. 7, the embodiment of the base member of the present invention is combined with the base 13 of a stapler. The embodiment of the lever member of the present invention is combined with the staple driving lever 14. To be consistent with the orientation introduced in the previous descriptions, the back end of the stapler base 13 is the end with the stapler anvil 12. The tongue 15 extends from the front end of the stapler base 13 and is used to wedge under the staple crossbar. The stapler base 13 is pivotally connected to the staple driving lever 14 by a pin 17 that provides a leverage fulcrum point. Tongue 15 may contain an optional groove 18 to indicate the point where the staple needs to be wedged up to for removal. The teeth 16 extends from the front end of the staple driving lever 14. The teeth 16 is narrow at tip 19 and wider at top section 20. FIG. 6 hows the staple driving lever 14 is at a first position where the teeth 16 is above the tongue 15 providing room to wedge a staple above the tongue 15. The front edges 21 of the teeth 16 are curved in such a way that when the staple driving lever 14 is moved into a second position where the tip 19 of teeth 16 is behind the staple point, the front edges 21 of the teeth 16 do not go below the baseline of the stapler base 13, and thus do not interfere with or damage the substrate.

FIG. 8 and FIG. 9 illustrate another embodiment of the present invention as attachments to a stapler device. To be consistent with the orientation introduced in the previous descriptions, the back end of the stapler base 23 is the end with the stapler anvil 22. A tongued member 25 is attached to the front end of the stapler base 23. A teethed member 26 is attached to the front end of the staple driving lever 24. Various means of attachment can be used to attach the tongued member 25 and teethed member 26 to the stapler device, such as strong bonding glue, rivets, welding or screws screwed into screw holes in the tongued member 25 and teethed member 26, or any other attachment means that is obvious to those skilled in the art. The stapler base 23 is pivotally connected to the staple driving lever 24 by a pin 29 that provides a leverage fulcrum point. A groove 30 can be optionally etched into tongue 27 to indicate the point where the staple needs to be wedged up to for removal. The teeth 28 extends from the front end of the teethed member 26. The teeth 28 is narrow at tip 31 and wider at top section 32. FIG. 8 shows the staple driving lever 24 is at a first position where the teeth 28 is above the tongue 27 providing room to wedge a staple above the tongue 27. The front edges 33 of the teeth 28 are curved in such a way that when the staple driving lever 24 is moved into a second position where the teeth 28 overlaps the tongue 27, the front edges 33 of the teeth 28 do not go below the baseline of the tongued member 25.

In the normal operation of a stapler device, lifting the staple driving lever of a stapler exposes the contents of the stapler, and is an operation used to refill the stapler. To prevent lifting the staple driving lever in the staple removing operation, another embodiment of the present invention is presented. FIG. 10 shows an embodiment of the present invention housed around a stapler device. A lever member 37 is housed around the staple driving lever 36, and can be moved independently from the staple driving lever 36. Thus when the user is operating the staple remover, the user does not need to move the staple driving lever 36 of a stapler. To be consistent with the orientation introduced in the previous descriptions, the back end of the stapler base 35 is the end with the stapler anvil 34. The tongue 38 extends from the front end of the stapler base 35 and is used to wedge under the staple crossbar.

The stapler base 35 is pivotally connected to the staple driving lever 36 by a pin 40 that provides a leverage fulcrum point. The lever member 37 is also pivotally connected by the pin 40. A groove 41 can be optionally etched into tongue 38 to indicate the point where the staple needs to be wedged up to for removal. The teeth 39 extends from the front end of the lever member 37. The teeth 39 is narrow at tip 42 and wider at top section 43. FIG. 10 shows the lever member 37 is at a first position where the teeth 39 is above the tongue 38 providing room to wedge a staple above the tongue 38. The front edges 44 of the teeth 39 are curved in such a way that when the lever member 37 is moved into a second position where the tip 42 of teeth 39 is behind the staple point, the front edges 33 of the teeth 39 do not go below the baseline of the stapler base 35, and thus do not interfere with or damage the substrate.

FIG. 22 illustrates another embodiment of the invention combined to the side of a stapler device. This embodiment of the invention can be combined to either or both sides of the stapler device, catering for either left-handed and/or right-handed users. This embodiment is similar to the embodiments presented in FIG. 6 except that the tongue 81 is located to the side of the front end of the stapler base 82, and the teeth 83 is located to the side of the front end of the staple driving lever 84. The advantage of this embodiment is that it is easier for the user to visually locate and manipulate the tongue 81 to wedge the tongue 81 under the staple crossbar.

The tongue 81 can be made as part of the stapler base 82, or as an attachment fixed to the stapler base 82. The teeth 83 can be made as part of the staple driving lever 84, or as an attachment fixed to the staple driving lever 84. Various means of attachments such as strong bonding glue, welding, rivet, screws, or any other attachment means that is obvious to those skilled in the art may be used.

A lever member 85 may also be pivotally connected to the staple driving lever 84 so that the lever member 85 can be moved independently of the staple driving lever 84 to prevent exposing the contents of the stapler. The lever member 85 can be pivotally connected to the staple driving lever 84 with a pin, or with rivets, or with any other methods obvious to those skilled in the art.

FIG. 11 to FIG. 15 shows another embodiment of the present invention where the distance between the teeth is narrower than the distance between the sides of the base member. In this case, it is important to provide a gap for the staple when the staple is removed. FIG. 11 and FIG. 12 illustrates an embodiment where the gap is provided by bending the base member 46 at the section 48 near the pin 47. An alternative way of providing the gap is with the use of washers 55 as shown in FIG. 13 and FIG. 14. FIG. 19 shows another alternative where the distance between the teeth is narrower than the distance between the sides of the lever member. It is also important to provide means to facilitate the passage of teeth 50 when the staple remover is operated. FIG. 11 to FIG. 14 shows an embodiment of the present invention where there are parallel grooves 54 in tongue 49 that facilitate the passage of teeth 50 when the lever 45 is lifted. FIG. 15 shows another variation where the tongue 56 is made narrower so that it is no wider than the distance between the teeth 50 of the lever member 45.

FIG. 19 to FIG. 21 illustrates other embodiment of the invention combined with a stapler device. The embodiments in FIG. 19 to FIG. 21 are very similar to the embodiments presented in FIG. 6, FIG. 8, and FIG. 10, respectively.

The main differences are: the distance separating the teeth 72; optional flange 80 in tongue 79; and optional notches 81 in teeth 72.

Referring to FIG. 19 to FIG. 21, the teeth 72 extends from front section of the lever member 73 such that right tooth 74 and left tooth 75 is closer to each other than the distance between both sides of the first section 76 of the said lever member 73 near the pivot point 77; the said teeth 72 also closer to each other than the distance between the legs of a staple used by the said stapler. The narrower distance between the teeth 72 allows both of the said teeth to go under the crossbar of the staple when in the staple removing operation. There are means to facilitate the passage of teeth 72 when the staple remover is operated, in this case, with parallel grooves 78 in the tongue 79. There is also an optional flange 80 protruding from the tongue 79 to prevent the staple from moving beyond the point where the staple can be removed. The flange assists in keeping the crossbar of the staple over the teeth 72 until most of the staple is removed. The same effect may also be achieved with optional notches 81 in teeth 72. The same effect may also be achieved by making the tongue wider after the point where the staple can be removed, where the wider width is larger than the distance between the legs of a staple, as shown the wider tongue 106 in FIG. 34.

The use of the wider tongue, the flange in the tongue and the notches in the teeth is not limited to this embodiment of the invention, but may be present in any embodiment of the invention. It should also be understood that any groove or depression in the tongue can be made by etching, moulding, bending the tongue or any other method known to those skilled in the art.

Figure 23:
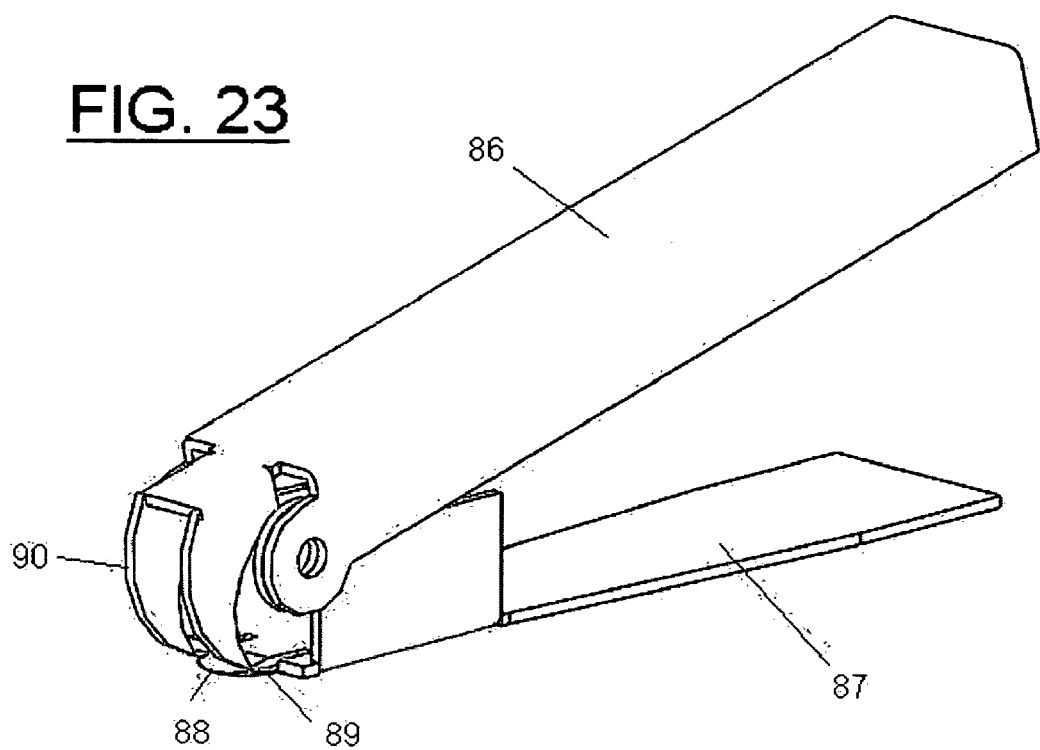
FIG. 23 shows an embodiment of the invention where the base member is thin.
Figure 24:
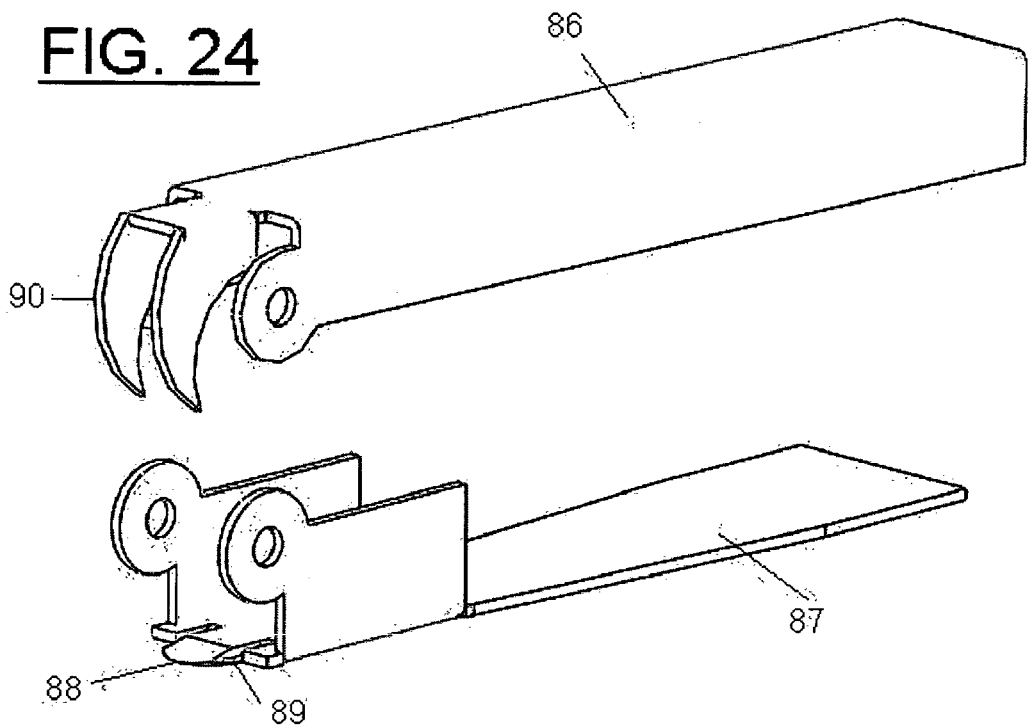
FIG. 24 shows an exploded view of embodiment of the invention where the base member is thin.

FIG. 23 to FIG. 28 illustrates embodiments of the invention which more similar to the lever member and base member of a stapler. The advantage of these embodiments is that they will only require inexpensive minor modifications to existing staplers. These embodiments may also be combined with a stapler as shown in the previous descriptions and illustrations. FIG. 23 and FIG. 24 illustrate a base member which is similar to the base member of a stapler, where the base member is thin. FIG. 25 to FIG. 28 illustrate a base member which is similar to the base member of a stapler, where the base member is folded to have more height.

Referring to FIG. 23 and FIG. 24, lever member 86 is pivotally connected to base member 87. The tongue 88 extends from the base member 87. The tongue 88 contains grooves 89 to facilitate the passage of teeth 90 when the level member 86 is moved from a first position to a second position.

Figure 25:
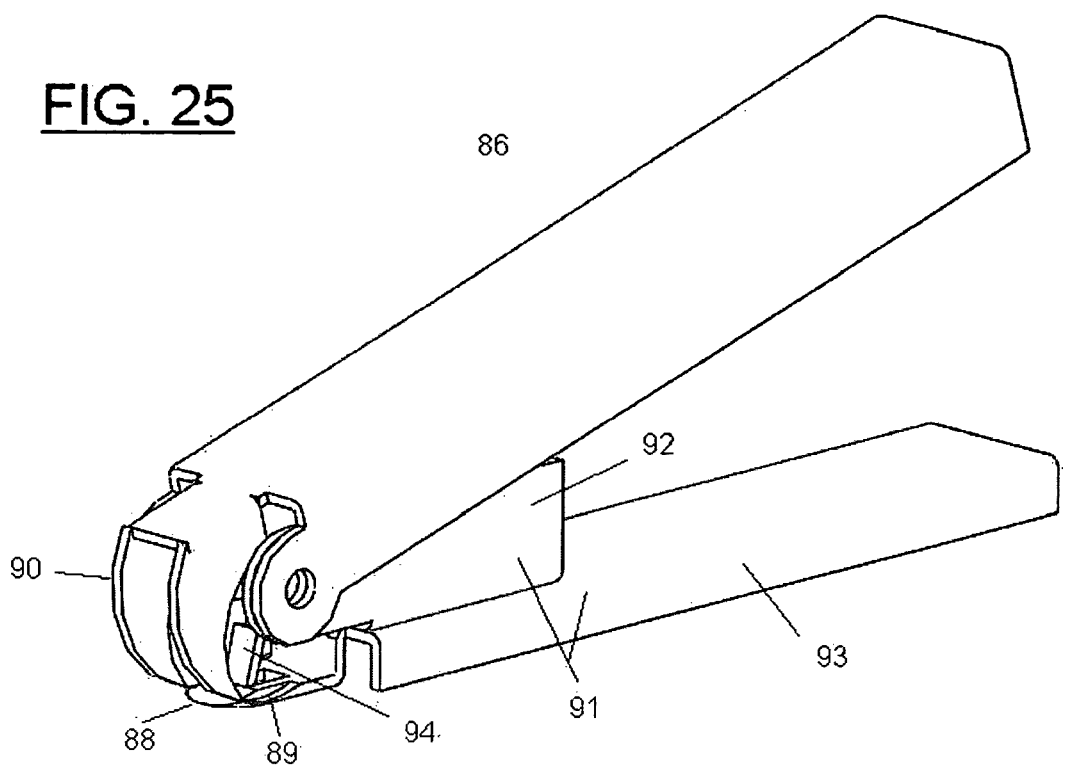
FIG. 25 shows an embodiment of the invention where the base member is folded to have height.
Figure 26:
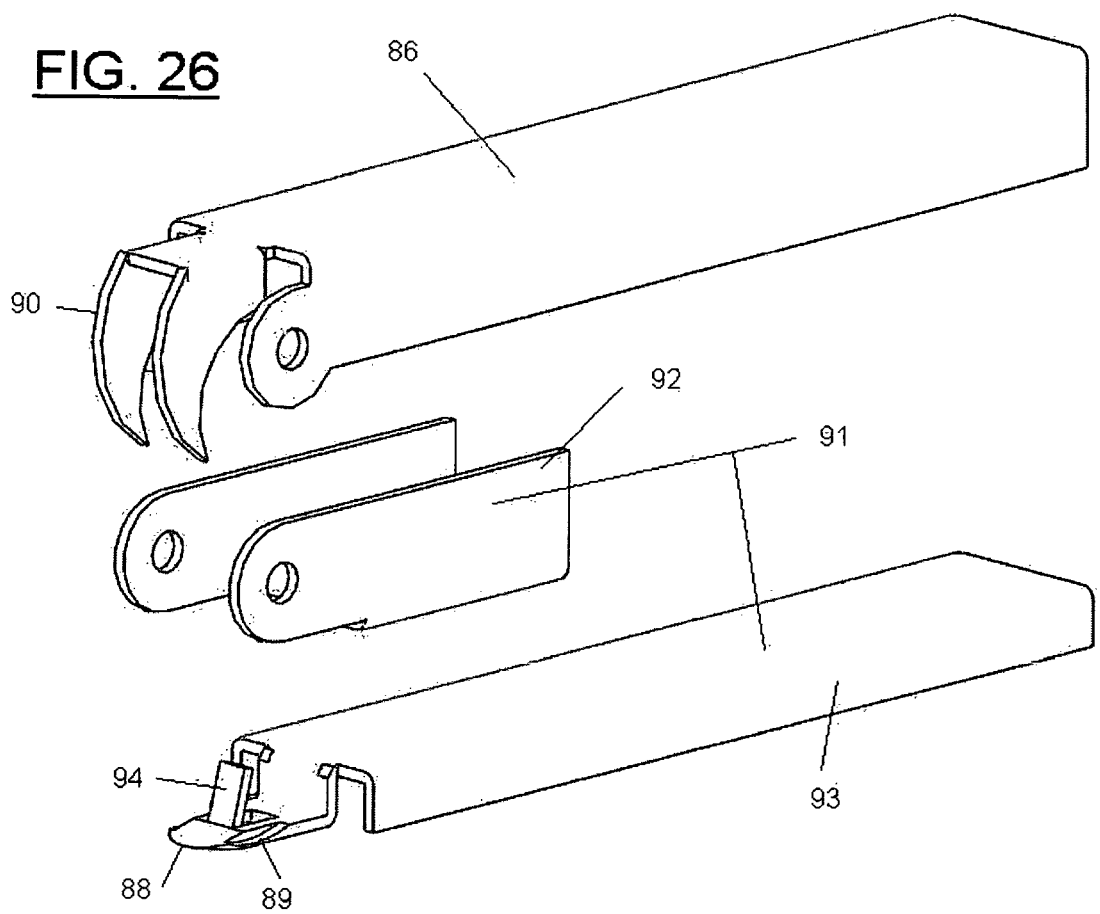
FIG. 26 shows an exploded view of embodiment of the invention where the base member is folded to have height.

Referring to FIG. 25 and FIG. 26, lever member 86 is pivotally connected to base member 91. The base member 91 comprises of a side member 92 and a folded member 93. The tongue 88 extends from the folded member 93 in base member 91. The tongue 88 contains grooves 89 to facilitate the passage of teeth 90 when the level member 86 is moved from a first position to a second position. The tongue 88 contains a flange 94 to prevent the staple from moving beyond the point where the staple can be removed.

Figure 27:
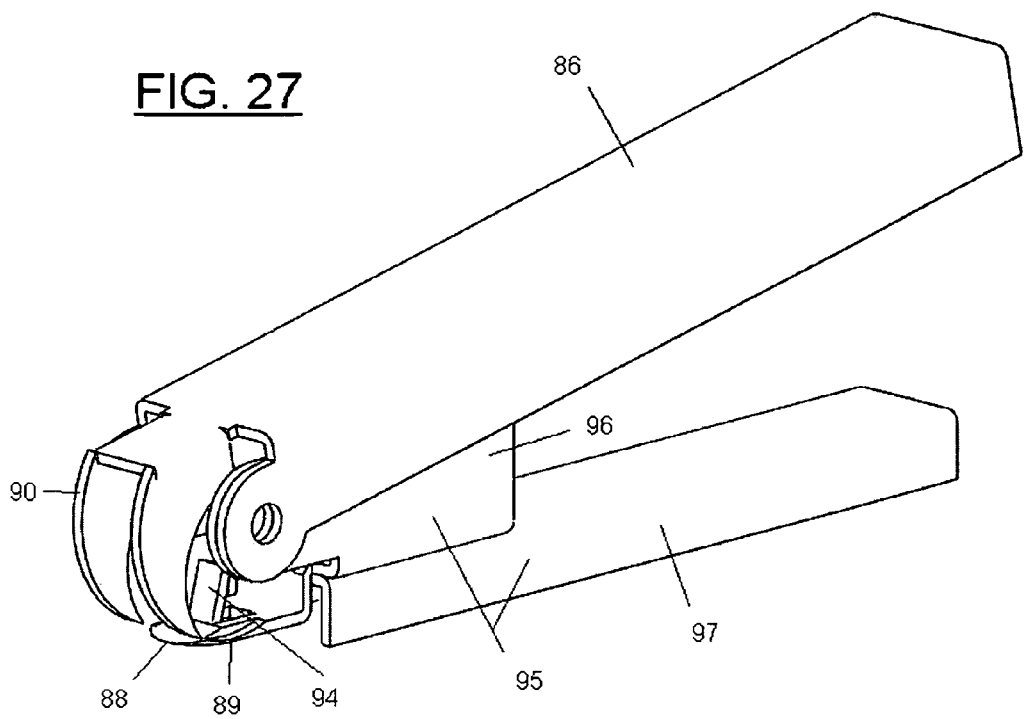
FIG. 27 shows another embodiment of the invention where the tongue extends from the side member.
Figure 28:
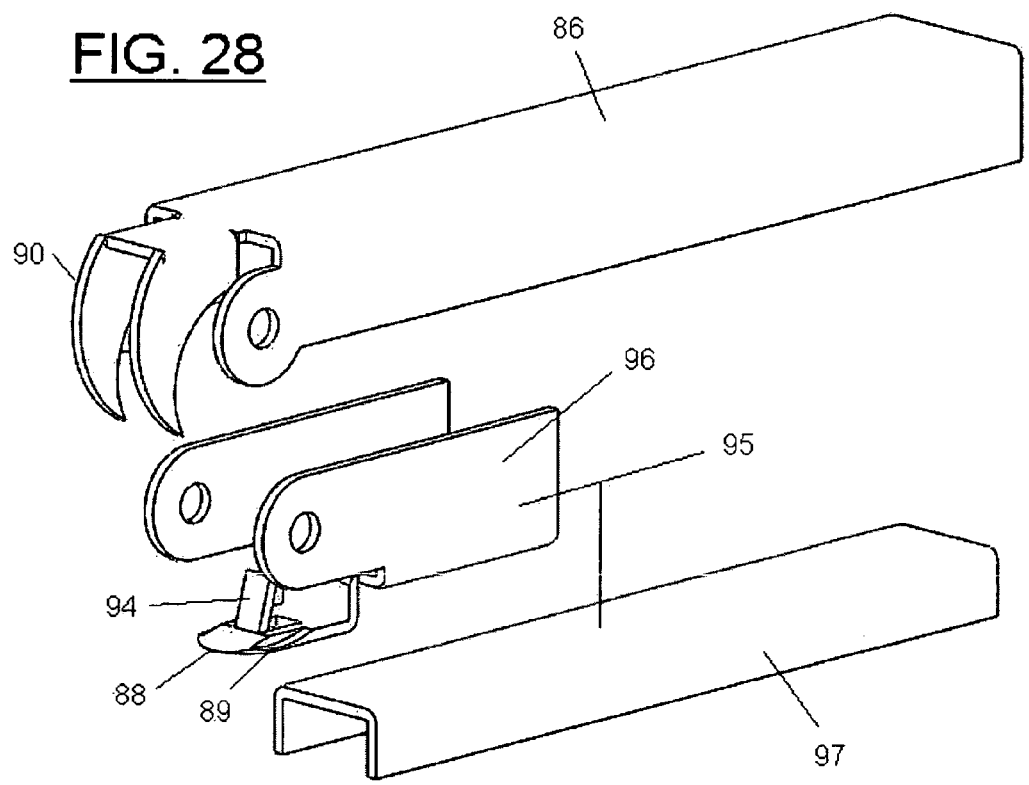
FIG. 28 shows an exploded view of the embodiment of the invention where the tongue extends from the side member.

Referring to FIG. 27 and FIG. 28, lever member 86 is pivotally connected to base member 95. The base member 95 comprises of a side member 96 and a folded member 97. The tongue 88 extends from the side member 96 in base member 95. The tongue 88 contains grooves 89 to facilitate the passage of teeth 90 when the level member 86 is moved from a first position to a second position. The tongue 88 contains a flange 94 to prevent the staple from moving beyond the point where the staple can be removed.

Figure 29:
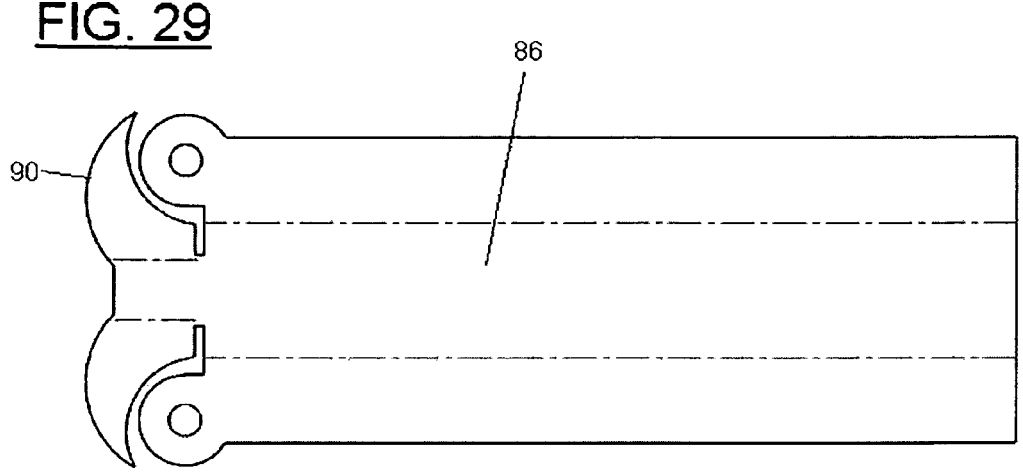
FIG. 29 shows the flattened lever member.
Figure 30:
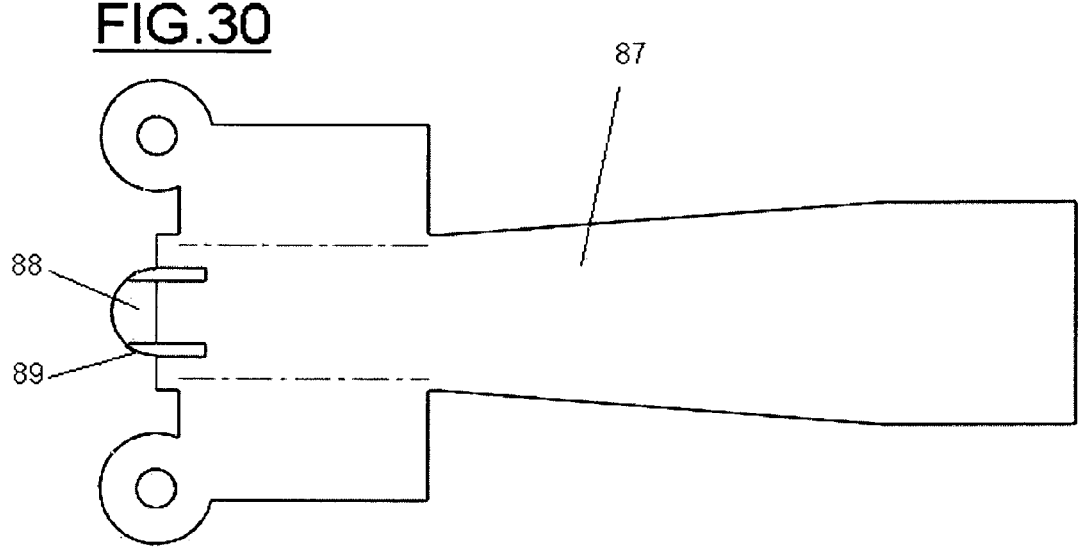
FIG. 30 shows the flattened thin base member.
Figure 31:
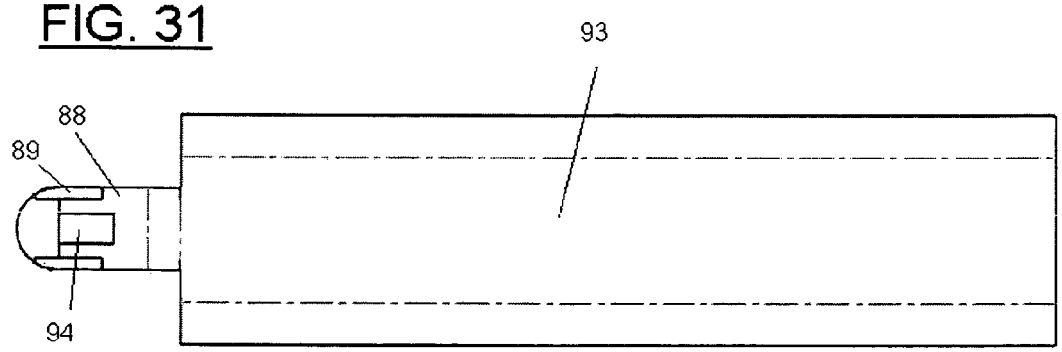
FIG. 31 shows the flattened base member which was folded to have height.
Figure 32:
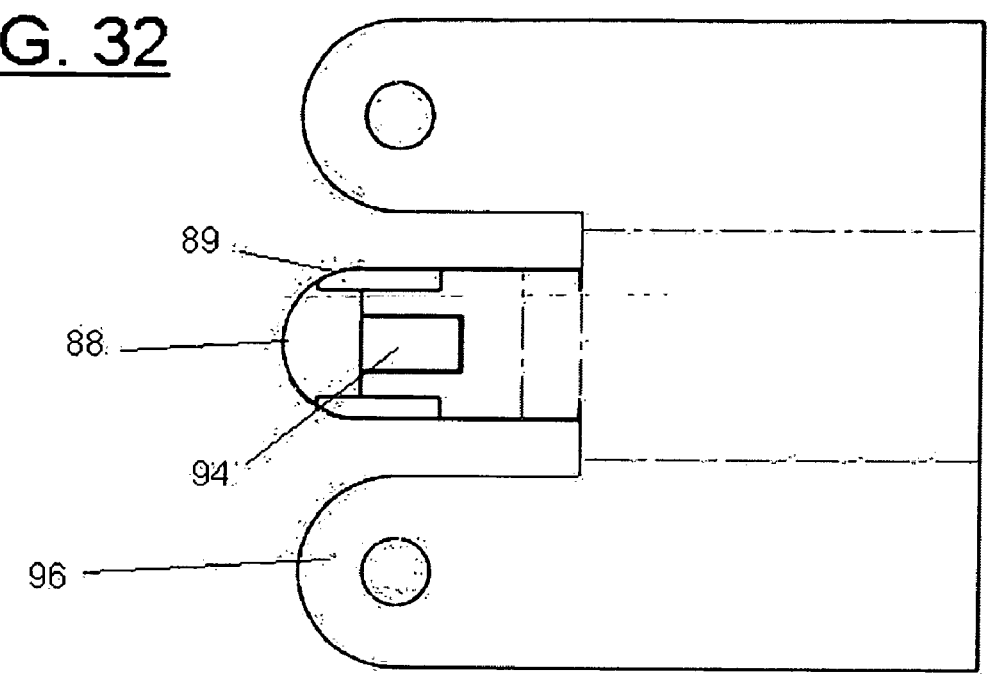
FIG. 32 shows the flattened side member.

FIG. 29 illustrate how the lever member 86 may be manufactured from a flat sheet of material. FIG. 30 illustrate how the base member 87 may be manufactured from a flat sheet of material. FIG. 31 illustrate how the folded member 93 may be manufactured from a flat sheet of material. FIG. 32 illustrate how the side member 96 may be manufactured from a flat sheet of material.

Figure 33:
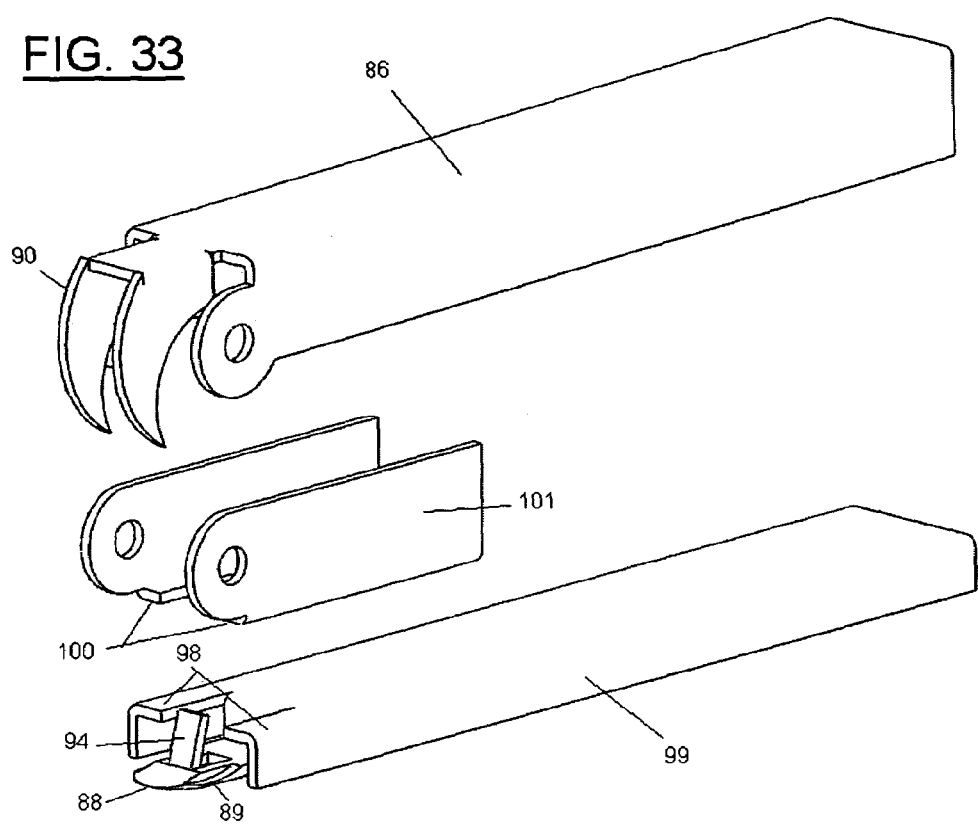
FIG. 33 shows an exploded view of an embodiment of the invention where the base member is folded to have height, and the tongue is partially covered.
Figure 34:
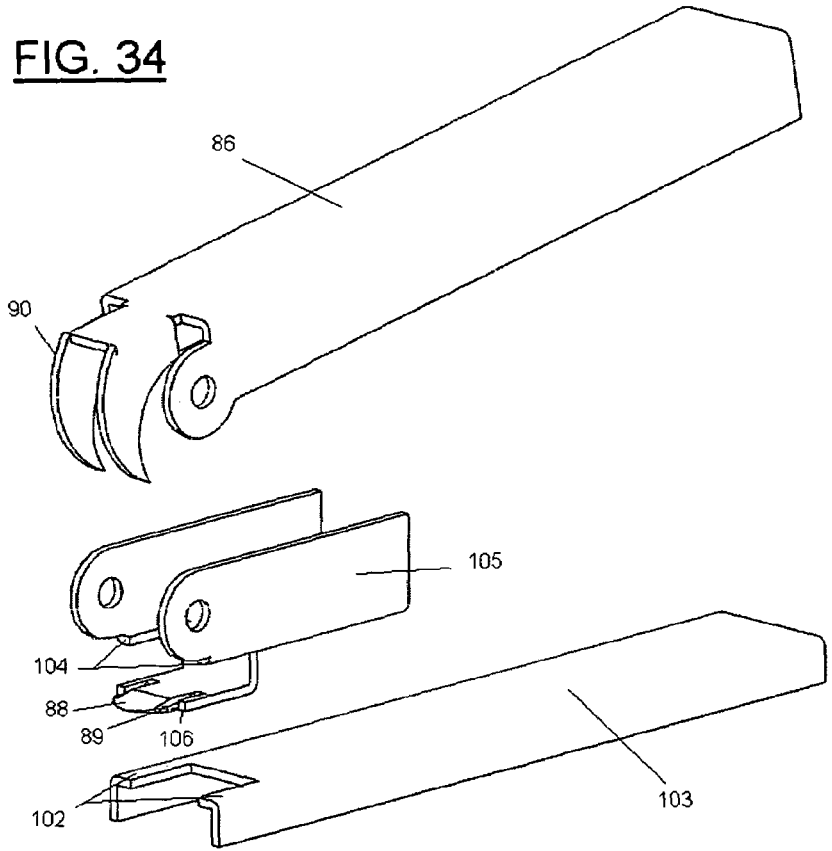
FIG. 34 shows an exploded view of the embodiment of the invention where the tongue extends from the side member, and the tongue is partially covered.

FIG. 33 and FIG. 34 illustrate further embodiments of the invention similar to the embodiments shown in FIG. 25 and FIG. 26, respectively. Referring to FIG. 33, the sides 98 of the folded member 99 partially or completely covers the tongue 88, making the invention less hazardous. The bottom sides 100 of the side member 101 may be extended to match the said sides 98 of folded member 99.

Similarly, referring to FIG. 34, the sides 102 of the folded member 103 partially or completely covers the tongue 88, making the invention less hazardous. The bottom sides 104 of the side member 105 may be extended to match the said sides 102 of folded member 103. FIG. 34 also illustrates the use of a wider tongue 106 after the staple point to prevent the staple from moving beyond where the staple can be removed.

Figure 35:
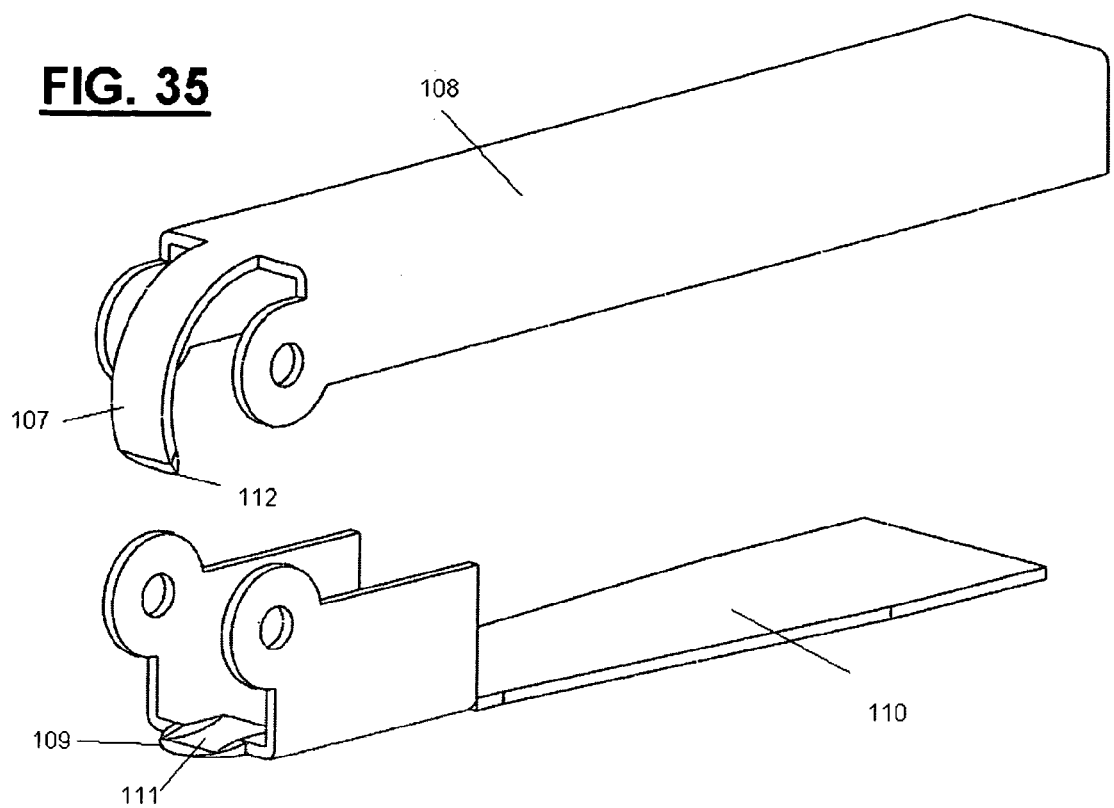
FIG. 35 shows an exploded view of an embodiment of the invention with a curved spade instead of teeth.
Figure 36:
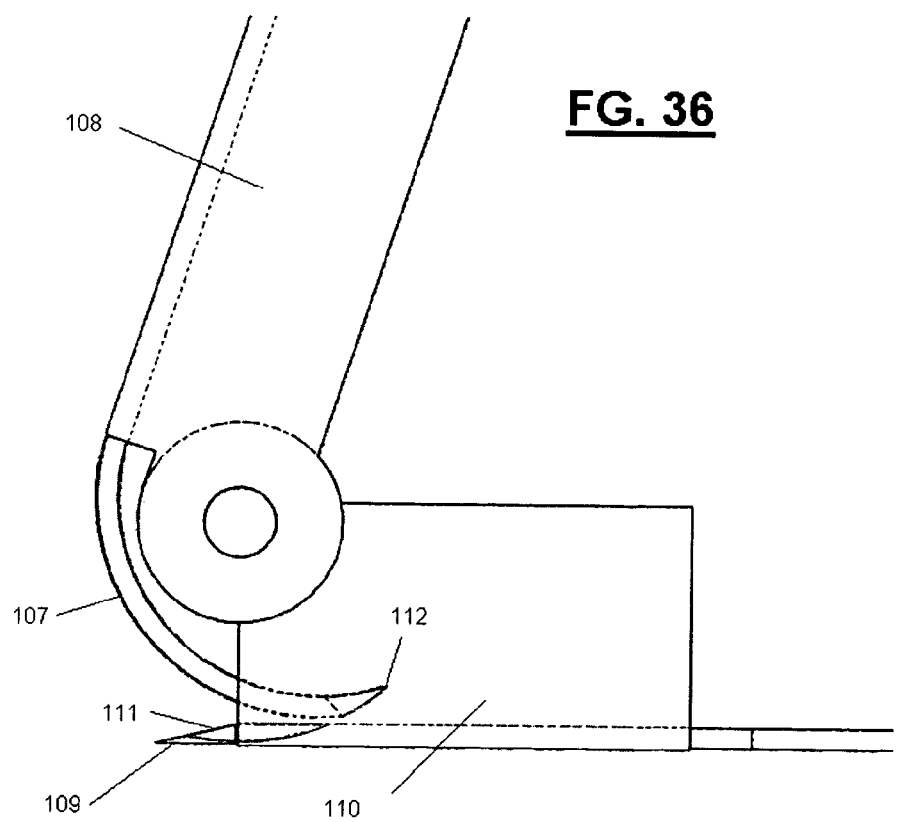
FIG. 36 shows a side view of the embodiment with a curved spade.

FIG. 35 and FIG. 36 shows another embodiment of the invention where a curved spade 107 instead of teeth is used to lift the staple from the substrate. The curved spade 107 extends from the front end of the lever member 108. A tongue 109 extends from the base member 110. Tongue 109 contains a wide groove 111 to facilitate the passage of the curved spade 107. The wide groove 111 may be created by etching, moulding or bending the tongue 109.

The curved spade 107 is curved in such a way that when the lever member 108 is moved from a first position where the curved spade 107 is above tongue 109, into a second position where the said tip 112 of the curved spade 107 is behind the staple point, the curved spade 107 engages the underside of the staple crossbar and lifts it from the substrate.

Thus, it should be understood that an embodiment of the invention is not limited to just using teeth to lift the staple from the substrate, but may use any means to lift the staple from the substrate using the leverage from the lever member pivotally connected to the base member.

Figure 16:
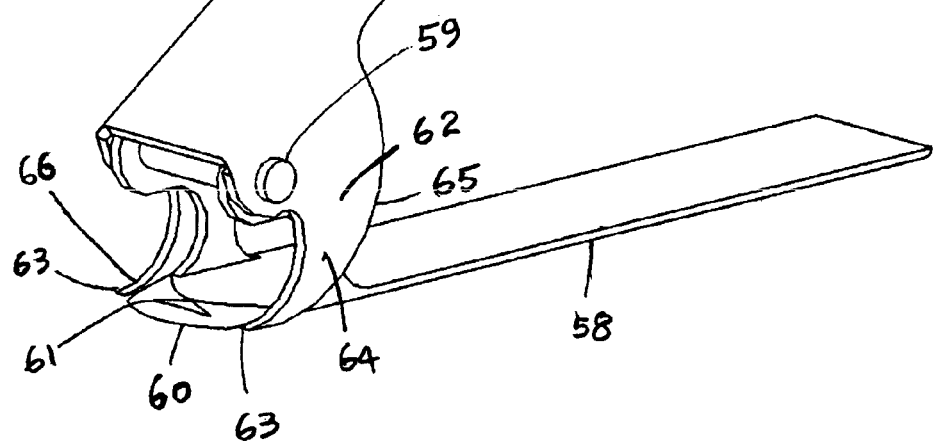
FIG. 16 shows an embodiment of the invention where the stapler remover is pushed instead of pulled.

FIG. 16 shows an embodiment of the present invention where the staple removing operation is performed by pushing the lever member 57 instead of lifting it. The base member 58 is pivotally connected to the lever member 57 by a pin 59 that provides a leverage fulcrum point. The tongue 60 extends from the front end of the base member 58 and is used to wedge under the staple crossbar. Tongue 60 contains an optional groove 61 to indicate the point where the staple needs to be wedged up to for removal. The teeth 62 extends from the front end of the lever member 57. The teeth 62 is narrow at tip 63 and wider at top section 64. FIG. 16 shows the lever member 57 is at a first position where the upper edge 66 of the tip 63 of teeth 62 is flush the top of the tongue 60. The back edges 65 of the teeth 62 are curved in such a way that when the lever member 57 is moved into a second position where the tip 63 of teeth 62 is well above the tongue 60, the back edges 65 of the teeth 62 do not go below the baseline of the base member 58, and thus do not interfere with or damage the substrate. Another variation of this embodiment of the present invention is where the lever member 57 fits inside the base member 58 and grooves are provided in the tongue 60 to facilitate the passage of teeth 62.

Figure 17:
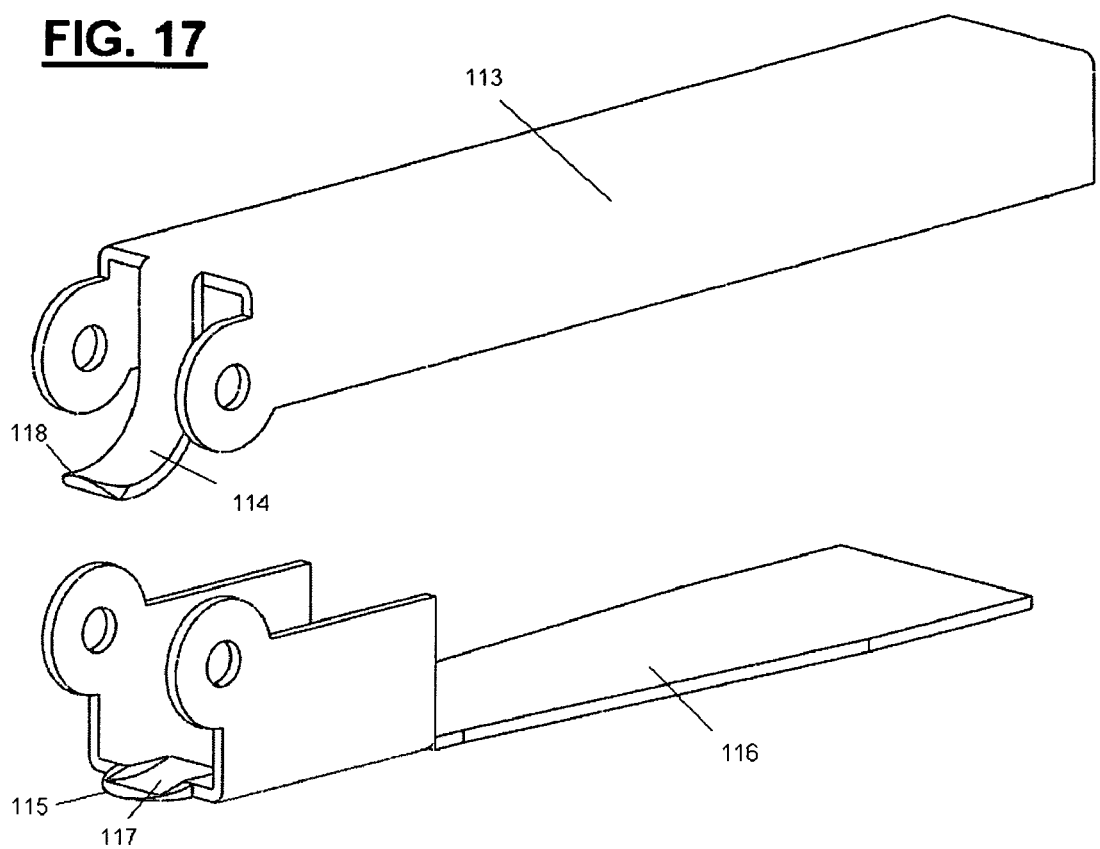
FIG. 17 shows an embodiment of the pushed remover using a curved spade instead of teeth.

FIG. 17 shows another embodiment where the staple removing operation is performed by pushing the lever member 113, but where a curved spade 114 instead of teeth is used to lift the staple from the substrate. The curved spade 114 extends from the front end of the lever member 113. A tongue 115 extends from the base member 116. Tongue 115 contains a wide groove 117 to facilitate the passage of the curved spade 114. The wide groove 117 may be created by etching, moulding or bending the tongue 115. The curved spade 114 is curved in such a way that when the lever member 113 is moved from a first position where the upper edge of the tip 118 of the curved spade 114 is flush with the top of the tongue 115, into a second position where the said tip 118 of the curved spade 114 is well above the tongue 115, the curved spade 114 engages the underside of the staple crossbar and lifts it from the substrate.

Figure 18:
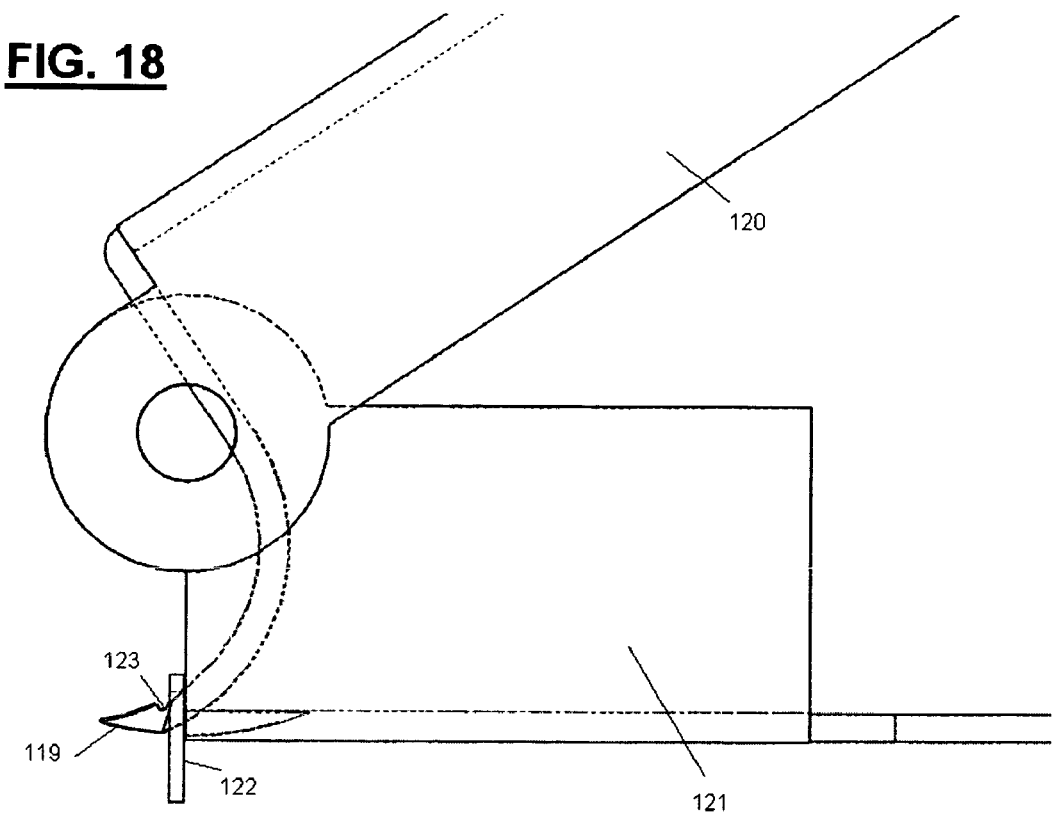
FIG. 18 is an enlarged side view of a pushed remover with the tongue on the lever member.

FIG. 18 shows another embodiment of the present invention where the staple removing operation is performed by pushing the lever member, and where a first tongue 119 extends from the lever member 120 is used to wedge under the staple crossbar. The front end of the base member 121 is next to the staple 122 and supports the substrate when the staple lifting operation is performed. For a base member that is folded to have more height, a second tongue that extends from the front end of the base member may be used to support the substrate. The first tongue 119 may also be combined with the teeth 62 in FIG. 16 to form a curved wedge, so that the back edges 65 will support the substrate. The first tongue 119 has an optional groove 123 to indicate to hold the staple when the lever member 120 is lifted.

The embodiments shown in FIG. 16, FIG. 17, and FIG. 18 may be combined with a stapler in the variations shown previously in this document, and may contains any optional components such as a groove or a flange in the tongue, or notches in the teeth.

It should be understood that an embodiment of this invention is not limited to the embodiments described in this document, and may also consists of any combination of the variations described in this document.

Also, an embodiment of the invention may be manufactured from any metal, ceramic alloy, carbon fibre, plastic, or any other material with suitable strength known to those in the art.

The claims defining the invention are as follows:

1. An apparatus for removing a staple from a substrate, the apparatus comprising:
   a base member having a front end, a rear end, and a first section near said front end, said base member further having a substantially flat surface for resting on the substrate during removal of the staple;
   a lever member having a front end, a rear end, and a first section near said front end, said first section of said lever member being pivotally joined to said first section of said base member;
   a tongue extending from said first section of said base member and parallel to said flat surface for wedging under a crossbar of the staple and supporting the substrate during removal of the staple;
   means for preventing the staple crossbar from moving beyond a point where the staple can be removed, said preventing means comprising a flange protruding from a middle of said tongue; and
   means for lifting the staple from the substrate using a leverage from said lever member when said lever member is rotated away from said base member, said lifting means joined to said first section of said lever member where said lifting means remains above said flat surface of said base member during the staple removing operation.

2. The apparatus of claim 1, further including means for increasing a friction of said base member to the substrate.

3. The apparatus of claim 2, wherein said friction increasing means comprises a rubber material joined to said flat surface of said base member.

4. The apparatus of claim 1, further comprising a groove in said tongue indicating a point where the staple can be removed.

5. The apparatus of claim 1, wherein said tongue extends from said front end of said base member.

6. The apparatus of claim 5, wherein said staple lifting means comprises teeth which extend from said front end of said lever member, such that when said lever member is moved from a first position where said teeth are above said tongue of said base member, to a second position where said teeth overlap said tongue, said teeth engage an underside of the staple crossbar and lifts the staple from the substrate, said teeth comprising front curved edges such that when said lever member is moved from said first position to said second position, said front edges of said teeth remain above said flat surface of said base member.

7. The apparatus of claim 6, wherein said lever member is a chambered member such that said base member fits inside said lever member in said first position.

8. The apparatus of claim 6, wherein said base member is a chambered member such that said lever member fits inside said base member and further comprising means for providing a gap between outer faces of said base member and inner faces of said lever member.

9. The apparatus of claim 8, wherein said gap providing means comprises said base lever being bent in a manner such that said base lever is wider at the base and narrower at the pivot point.

10. The apparatus of claim 8, wherein said tongue of base member contains grooves to facilitate a passage of said teeth of said lever member in said second position.

11. The apparatus of claim 8, wherein a width of said tongue is less than a distance between said teeth.

12. The apparatus of claim 5, wherein said staple lifting means comprises teeth which extend from said front end of said lever member, such that when said lever member is moved from a first position where an upper edge of a tip of the said teeth is flush with an upper edge of said tongue, to a second position where said tip of said teeth is above said tongue, said teeth engage an underside of the staple crossbar and lifts the said staple from the substrate, bottom edges of said teeth being curved such that when said lever member is moved from said first position to said second position, said bottom edges of said teeth remain above said flat surface of said base member.

13. The apparatus of claim 12, including means for biasing said lever member away from said base member into said first position.

14. The apparatus of claim 13, wherein said biasing means comprises a spring positioned between said lever member and said base member.

15. The apparatus of claim 12, wherein said lever member is a chambered member such that said base member fits inside said lever member.

16. The apparatus of claim 12, wherein said base member is a chambered member such that said lever member fits inside said base member.

17. The apparatus of claim 16, wherein said tongue of said base member contain grooves to facilitate a passage of said teeth of said lever member.

18. The apparatus of claim 16, wherein said tongue is less than a distance between said teeth of said lever member.

19. An apparatus for removing a staple from a substrate, the apparatus comprising:
a stapler for driving the staple into the substrate, said stapler comprising a stapler base having a front end, a rear end and a substantially flat surface for resting on the substrate; and a staple driving lever having a front end and a rear end, said staple driving lever pivotally joined to said stapler base, where said rear end of said stapler base and said stapler lever is the staple driving end;
a tongue extending from said front end of the said stapler base and substantially parallel to said flat surface for wedging under a crossbar of the staple, said tongue supporting the substrate during removal of the staple;
means for preventing the staple crossbar from moving beyond a point where the staple can be removed, said preventing means comprising a flange protruding from a middle of said tongue; and
a staple lifting means comprising teeth which extend from said front end of said staple driving lever, such that when said staple driving lever is moved from a first position adjacent to said stapler base where said teeth are above said tongue of said stapler base, to a second position away from said stapler base where said teeth overlap said tongue, said teeth engage an underside of the staple crossbar and lifts the staple from the substrate, front edges of said teeth being curved such that when said staple driving lever is moved from said first position to said second position, said front edges of said teeth remain above said flat surface of said stapler base.

20. An apparatus for removing a staple from a substrate, the apparatus comprising:
a stapler for driving the staple into the substrate, said stapler comprising a stapler base having a front end, a rear end and a substantially flat surface for resting on the substrate; and a staple driving lever having a front end and a rear end, said staple driving lever pivotally joined to said stapler base, where said rear end of said stapler base and said stapler lever is the staple driving end;
a tongued member joined to said front end of said stapler base of said stapler and parallel to said flat surface;
a teethed member joined to said front end of said staple driving lever of said stapler, said teethed member comprising teeth having curved front edges;
a tongue extending from the front end of said tongued member for wedging under a crossbar of the staple;
means for preventing the staple crossbar from moving beyond a point where the staple can be removed, said preventing means comprising a flange protruding from a middle of said tongue; and
a staple lifting means comprising said teethed member joined to said front end of said staple driving lever, such that when said staple driving lever is moved from a first position where said teeth member is above said tongue of said tongued member, to a second position where said teeth overlap said tongue, said teeth engages an underside of the staple crossbar and lifts the staple from the substrate, said teeth remaining above said flat surface during said lifting of the staple.

21. An apparatus for removing a staple from a substrate, the apparatus comprising:
a stapler for driving the staple into the substrate, said stapler comprising a stapler base having a front end, a rear end and a substantially flat surface for resting on the substrate; and a staple driving lever having a front end and a rear end, said staple driving lever pivotally joined to said stapler base, where said rear end of said stapler base and said stapler lever is the staple driving end;
a chambered lever member that houses said staple driving lever of said stapler;
a tongue extending from said front end of said stapler base and substantially parallel to said flat surface for wedging under a crossbar of the staple, said tongue supporting the substrate during removal of the staple;

means for preventing the staple crossbar from moving beyond a point where the staple can be removed, said preventing means comprising a flange protruding from a middle of said tongue; and a staple lifting means teeth which extend from said front end of said staple driving lever, such that when staple driving lever is moved from a first position where said teeth are above said tongue of said stapler base, to a second position where said teeth overlap said tongue, said teeth engage an underside of the staple crossbar and lifts the staple from the substrate, front edges of said teeth being curved such that when said staple driving lever is moved from said first position to said second position, the said front edges of said teeth remain above said flat surface.

22. An apparatus for removing a staple from a substrate, the apparatus comprising:

a stapler for driving the staple into the substrate, said stapler comprising a stapler base having a front end, a rear end and a substantially flat surface for resting on the substrate; and a staple driving lever having a front end and a rear end, said staple driving lever pivotally joined to said stapler base, where said rear end of said stapler base and said stapler lever is the staple driving end;

a tongue extending from said front end of the said stapler base and substantially parallel to said flat surface for wedging under a crossbar of the staple, said tongue supporting the substrate during removal of the staple;

means for preventing the staple crossbar from moving beyond a point where the staple can be removed, said preventing means comprising a flange protruding from a middle of said tongue; and a staple lifting means comprising teeth which extend from said front end of said staple driving lever, such that when said staple driving lever is moved from a first position where an upper edge of a tip of the said teeth is flush with an upper edge of said tongue, to a second position where said tip of said teeth is above said tongue, said teeth engage an underside of the staple crossbar and lifts the staple from the substrate, bottom edges of said teeth being curved such that when said staple driving lever is moved from said first position to said second position, said bottom edges of said teeth remain above said flat surface of said stapler base.

23. An apparatus for removing staples comprising:

a stapler for driving the staple into the substrate, said stapler comprising a stapler base having a front end, a rear end and a substantially flat surface for resting on the substrate; and a staple driving lever having a front end and a rear end, said staple driving lever pivotally joined to said stapler base, where said rear end of said stapler base and said stapler lever is the staple driving end;

a tongued member joined to said front end of said stapler base of said stapler and parallel to said flat surface;

a teethed member joined to said front end of said staple driving lever of said stapler, said teethed member comprising teeth having curved front edges;

a tongue extending from the front end of said tongued member for wedging under a crossbar of the staple;

means for preventing the staple crossbar from moving beyond a point where the staple can be removed, said preventing means comprising a flange protruding from a middle of said tongue; and a staple lifting means comprising said teethed member joined to said front end of said staple driving lever, such that when said staple driving lever is moved from a first position where an upper edge of a tip of the said teeth is flush with an upper edge of said tongue, to a second position where said tip of said teeth is above said tongue, said teeth engages an underside of the staple crossbar and lifts the said staple from the substrate, bottom edges of said teeth being curved such that when said stapler driving lever is moved from said first position to said second position, said bottom edges of said teeth remain above said flat surface.

24. An apparatus for removing staples comprising:

a stapler for driving the staple into the substrate, said stapler comprising a stapler base having a front end, a rear end and a substantially flat surface for resting on the substrate; and a staple driving lever having a front end and a rear end, said staple driving lever pivotally joined to said stapler base, where said rear end of said stapler base and said stapler lever is the staple driving end;

a chambered lever member that houses said staple driving lever of said stapler;

a tongue extending from said front end of said stapler base and substantially parallel to said flat surface for wedging under a crossbar of the staple, said tongue supporting the substrate during removal of the staple;

means for preventing the staple crossbar from moving beyond a point where the staple can be removed, said preventing means comprising a flange protruding from a middle of said tongue; and staple lifting means comprising teeth which extend from said front end of said staple driving lever, such that when said staple driving lever is moved from a first position where an upper edge of said teeth is flush with an upper edge of said tongue, to a second position where said teeth are above said tongue, said teeth engage an underside of the staple crossbar and lifts the staple from the substrate, bottom edges of said teeth being curved such that when staple driving lever is moved from said first position to said second position, said bottom edges of said teeth remain above said flat surface.

25. The apparatus of claim 24, including means for biasing said staple driving lever away from said stapler base into said first position.

26. The apparatus of claim 25, wherein said biasing means comprises a spring positioned between said staple driving lever and said stapler base.

27. An apparatus for removing a staple from a substrate, the apparatus comprising:

a base member having a front end, a rear end, and a first section near said front end;

a lever member having a front end, a rear end, and a first section near said front end, said first section of the lever member is pivotally attached to said first section of said base member;

means for wedging under the staple crossbar, said wedging means comprising a tongue;

means for preventing the staple crossbar from moving beyond a point where the staple can be removed, said preventing means comprising a flange protruding from a middle of said tongue;

means for lifting the staple from the substrate using leverage from said lever member pivotally attached to said base member, where said lifting means does not extend below a baseline of said base member during the staple removing operation; and means for supporting and continuing to support the substrate throughout the staple removing operation with said base member.

28. An apparatus for removing a staple from a substrate, the apparatus comprising:

base member means for resting on the substrate;

lever means for joining to said base member means;

means for wedging under a crossbar of the staple;

means for preventing the staple crossbar from moving beyond a point where the staple can be removed, said preventing means comprising a flange protruding from a middle of said wedging means; and means for lifting the staple from the substrate.

29. An apparatus for removing a staple from a substrate, the apparatus comprising:

means for driving the staple into the substrate;

means for wedging under a crossbar of the staple;

means for preventing the staple crossbar from moving beyond a point where the staple can be removed, said preventing means comprising a flange protruding from a middle of said wedging means; and means for lifting the staple from the substrate.

* * * * *